US012135818B1

(12) United States Patent
Peruzzi et al.

(10) Patent No.: US 12,135,818 B1
(45) Date of Patent: Nov. 5, 2024

(54) INTEGRATED COMMUNICATION SYSTEM

(71) Applicant: Health-E-Communication, Inc., Chicago, IL (US)

(72) Inventors: William Peruzzi, Chicago, IL (US); Juan Aguirre, Coral Gables, FL (US)

(73) Assignee: Health E-Communication, Inc., Chicago, IL (US)

( * ) Notice: Subject to any disclaimer, the term of this patent is extended or adjusted under 35 U.S.C. 154(b) by 0 days.

(21) Appl. No.: 18/467,568

(22) Filed: Sep. 14, 2023

Related U.S. Application Data

(63) Continuation-in-part of application No. 17/032,484, filed on Sep. 25, 2020, now abandoned.

(60) Provisional application No. 62/907,100, filed on Sep. 27, 2019, provisional application No. 62/994,733, filed on Mar. 25, 2020.

(51) Int. Cl.
*H04L 29/06* (2006.01)
*G06F 21/62* (2013.01)
*G16H 40/67* (2018.01)
*G16H 80/00* (2018.01)
*H04L 9/08* (2006.01)

(52) U.S. Cl.
CPC ......... *G06F 21/6245* (2013.01); *G16H 40/67* (2018.01); *G16H 80/00* (2018.01); *H04L 9/0825* (2013.01)

(58) Field of Classification Search
CPC .... G06F 21/6245; G16H 40/67; G16H 80/00; H04L 9/0825
USPC ......................................................... 726/28
See application file for complete search history.

(56) References Cited

U.S. PATENT DOCUMENTS

| | | | |
|---|---|---|---|
| 6,523,009 | B1 | 2/2003 | Wilkins |
| 6,874,085 | B1 | 3/2005 | Koo et al. |
| 6,988,075 | B1 | 1/2006 | Hacker |
| 7,983,934 | B1 | 7/2011 | Sholtis et al. |
| 10,832,823 | B1 | 11/2020 | Lippoff et al. |
| 2001/0041991 | A1 | 11/2001 | Segal et al. |

(Continued)

FOREIGN PATENT DOCUMENTS

KR   2012-0086899 A   8/2012

OTHER PUBLICATIONS

H. Tabenkin et al., "Referrals of patients by family physicians to consultatnts: a survey of the Israeli Family Practice Research Network," Family Practice, vol. 15, No. 2, Apr. 1998, pp. 158-164.

*Primary Examiner* — Jeffrey C Pwu
*Assistant Examiner* — Nega Woldemariam
(74) *Attorney, Agent, or Firm* — Knobbe, Martens, Olson & Bear, LLP

(57) ABSTRACT

A cloud-based, secure, integrated communication system for patient care delivery system can provide a platform that is device-agnostic and can adapt to the technology chosen by users of the system. The system can allow for asynchronous and/or real-time communication among all participants. Patients can create and manage their own specific health issues. Patients can assign their own caregivers and/or approve new care providers. Patients can also control whether to include certain members of the family and/or friends in discussions regarding the patients' health issues. Physicians can engage other healthcare providers, advanced practitioners, and/or consultants with specific patient issues. The system can also assist with billing for eligible e-visits for insurers providing such reimbursable services.

12 Claims, 30 Drawing Sheets

(56) References Cited

U.S. PATENT DOCUMENTS

| | | |
|---|---|---|
| 2003/0037054 A1 | 2/2003 | Dutta et al. |
| 2003/0158754 A1 | 8/2003 | Elkind |
| 2003/0177030 A1 | 9/2003 | Turner et al. |
| 2003/0177033 A1 | 9/2003 | Park et al. |
| 2003/0233258 A1 | 12/2003 | Cottrell et al. |
| 2004/0078211 A1 | 4/2004 | Schramm-Apple et al. |
| 2004/0167875 A1 | 8/2004 | Sneiders |
| 2004/0199765 A1 | 10/2004 | Kohane et al. |
| 2004/0260658 A1 | 12/2004 | Dettinger et al. |
| 2005/0027560 A1 | 2/2005 | Cook |
| 2005/0209891 A1 | 9/2005 | Jacobus et al. |
| 2006/0058626 A1 | 3/2006 | Weiss et al. |
| 2006/0123347 A1 | 6/2006 | Hewitt et al. |
| 2006/0206361 A1 | 9/2006 | Logan, Jr. |
| 2006/0259331 A1 | 11/2006 | Lurtz et al. |
| 2007/0027720 A1 | 2/2007 | Hasan et al. |
| 2007/0041626 A1 | 2/2007 | Weiss et al. |
| 2007/0192137 A1 | 8/2007 | Ombrellaro |
| 2007/0282629 A1 | 12/2007 | Plambeck |
| 2008/0021786 A1 | 1/2008 | Stenberg et al. |
| 2008/0034439 A1 | 2/2008 | Chen et al. |
| 2008/0086337 A1 | 4/2008 | Soon-Shiong |
| 2009/0164252 A1 | 6/2009 | Morris et al. |
| 2011/0046976 A1 | 2/2011 | Peruzzi |
| 2012/0278100 A1 | 11/2012 | Macoviak |
| 2016/0098522 A1 | 4/2016 | Weinstein |
| 2020/0084186 A1* | 3/2020 | Yang ................ H04L 67/01 |

\* cited by examiner

Invitations

| Received | Sent | Surrogate | Surrogate Authorizer | | |
|---|---|---|---|---|---|
| Action | Date ◆ | Sent to ◆ | Relationship ◆ | Status ◆ |
| | 08 27, 2019 2:01PM | Provider 5 | Providers | Accepted |
| | 08 18, 2019 3:59PM | Provider 4 | Providers | Accepted |
| | 08 04, 2019 6:43PM | Caregiver 1 | Companion Caregiver | Accepted |
| | 03 30, 2019 6:41PM | Family 3 | Family & Friends | Accepted |
| | 08 30, 2019 5:48PM | Provider 3 | Providers | Accepted |
| | 08 05, 2019 9:08AM | Family 2 | Family & Friends | Accepted |
| | 02 12, 2019 7:39AM | Provider 2 | Providers | Accepted |
| | 02 11, 2019 10:38PM | Family 1 | Family & Friends | Accepted |
| | 02 11, 2019 10:37PM | Caregiver Patient | | Accepted |
| | 02 12, 2019 6:54AM | Provider 1 | Providers | Accepted |

INTEGRATED COMMUNICATION SYSTEM

BACKGROUND

The present disclosure is related to an integrated web-based communication system that facilitates more efficient and/or secure communication between and among users who require secure, and multifaceted communication structures, in particular, in the healthcare context.

SUMMARY

The present disclosure is related to an integrated web-based communication system configured to improve healthcare collaboration by a designated surrogate of a patient. The system can comprise a database configured to store a plurality of user accounts, users of the system comprising at least a patient, a primary healthcare provider of the patient, and one or more designated surrogates of the patient, wherein accounts of the patient, the primary healthcare provider, and the one or more designated surrogates can be interconnected so as to allow asynchronous communication among one or more of the patient, the primary healthcare provider, or the one or more surrogates; and in response to receiving a request to activate surrogacy, a computer processor configured to asynchronously: send an electronic message relating to the request to a user device of the patient; send alert message(s) to user device(s) of one or more designated surrogates on the patient's account; receive an instructions message of accepting surrogacy duty from one of the one or more designated surrogate who accepted surrogacy duty; and update the patient's account in the database to change a status of the designated surrogate who accepted surrogacy duty to an acting surrogate in response to the received instructions message.

In some configurations, in response to the request to activate surrogacy being received from a user device of one of the one or more designated surrogates, the processor can be configured to send an alert message to a user device of the primary healthcare provider and obtain an approval message from the user device of the primary healthcare provider, wherein the primary healthcare provider can act as a surrogacy authorizer.

In some configurations, the processor can be configured to prompt the primary healthcare provider to review, on the user device of the primary healthcare provider, the patient's surrogacy document and the requesting surrogate's medical condition.

In some configurations, wherein, in response to the request to activate surrogacy being received from a user device of the primary healthcare provider, the processor can be configured to send an alert to all the user device(s) of the one or more designated surrogates, wherein the primary healthcare provider can act as a surrogacy authorizer.

In some configurations, the processor can be configured to automatically select a primary designated surrogate to carry out surrogacy duty unless a user device of the primary designated surrogate sends a refusal message or does not respond to the alert message.

In some configurations, the processor can be configured to terminate the request to activate surrogacy in response to receiving instructions from the user device of the patient that surrogacy be canceled.

In some configurations, the patient's contact with the one or more designated surrogates can be established in the database in response to the processor receiving an invitation from the user device of the patient to be sent to a user device of a surrogate candidate.

In some configurations, in response to receiving the invitation from the user device of the patient, the processor can be configured to send the invitation to the user device of the surrogate candidate and send a separate invitation to a user device of the primary healthcare provider, wherein the primary healthcare provider can act as a surrogacy authorizer.

In some configurations, the processor can be configured to prompt the patient to upload to the database a surrogate document prior to inviting a surrogate.

In some configurations, the processor can be configured to prompt the invited surrogate candidate to register as a user of the system in response to the invited surrogate candidate not having an account in the database.

In some configurations, the processor can be further configured to receive instructions about caring for the patient from a user device of the acting surrogate.

The present disclosure provides an integrated communication system configured to improve healthcare collaboration by a consultant. The system can comprise a database configured to store a plurality of user accounts, users of the system comprising at least a patient, a primary healthcare provider of the patient, and a consultant, wherein at least accounts of the patient and the primary healthcare provider can be interconnected so as to allow asynchronous communication between the patient and the primary healthcare provider; and in response to receiving a request to invite a consultant from a user device of the provider, a computer processor configured to asynchronously: send an electronic message relating to the request to a user device of the patient; send an alert of the invitation to a user device of the consultant in response to a permission message received from the user device of the patient; and update the database to establish a patient-consultant contact between the patient's account and the consultant's account in response to receiving an acceptance of the invitation from the user device of the consultant.

In some configurations, the patient's account includes at least one active health issue, the patient-consultant contact giving the consultant's account permission to view one of the at least one active health issue for which the invitation is made.

In some configurations, the consultant's account is not permitted to view other ones of the at least one active healthcare on the patient's account.

In some configurations, the processor is configured to terminate the request in response to receiving instructions from the user device of the patient to decline inviting the consultant.

In some configurations, the processor is configured to receive, process, and post a comment received from the user device of the patient, the processor further configured to send alerts of the posting of the comment to the user devices of the provider and the consultant.

In some configurations, the processor is configured to receive, process, and post a reply comment received from the user devices of the provider and/or the consultant.

In some configurations, the processor is configured to post the reply comment as a public or private comment in response to instructions received from the user device of the patient.

The present disclosure provides an integrated communication system configured to improve healthcare collaboration by a covering provider when a primary healthcare provider is unavailable. The system can comprise a database configured to store a plurality of user accounts, users of the system comprising at least a patient, a primary healthcare provider of the patient, and a covering provider, wherein at least accounts of the patient and the primary healthcare provider can be interconnected so as to allow asynchronous communication between the patient and the primary healthcare provider; and in response to a status of being unavailable in the primary healthcare provider's account, a computer processor configured to asynchronously: determine whether the patient's account in the database has an active health topic; send an electronic message to a user device of the patient notifying the patient of the covering provider in response to the patient's account having an active health topic; send an invitation to a user device of the covering provider in response to instructions from the user device of the patient accepting the covering provider; and update the database to establish a patient-covering provider contact between the patient's account and the covering provider's account in response to instructions from the user device of the covering provider accepting the invitation.

In some configurations, the processor can be configured to send an alert to the user device of the covering provider in response to the patient's account indicating that an event related to the active health topic has occurred.

In some configurations, the processor can be further configured to send an alert to a user device of the primary healthcare provider that the event related to the active health topic has occurred.

In some configurations, the processor can be configured to terminate the patient-covering provider contact in response to an electronic message from the user device of the primary healthcare provider that the primary healthcare provider is available.

In some configurations, the processor can be configured to send a coverage request from the primary healthcare provider to the user device of the covering provider prior to the status of being unavailable in the primary healthcare provider's account.

In some configurations, in response to the patient having no active health topic, the processor can be configured to send an electronic message to the user device of the patient notifying the patient that the covering provider has been assigned when a new topic is created in the patient's account.

The present disclosure provides an integrated communication system configured to improve healthcare collaboration by a parent patient of a child patient. The system can comprise a database configured to store a plurality of user accounts, users of the system comprising at least first and second patients, and a primary healthcare provider of the patient, wherein accounts of the first and/or second patient and the primary healthcare provider can be interconnected so as to allow asynchronous communication between the first and/or second patient and the primary healthcare provider; and a computer processor configured to asynchronously: create a child account in the database in response to instructions received from a user device of the first patient, the first patient being a first guardian of a child; automatically add at least a portion of the first patient account's profile information to the child account; create a parent-child contact between the first patient's account and the child account in the database; and permit the first patient's account to login to the child account for parental access and/or switch back to the first patient's account.

In some configurations, the processor can be further configured to send an invitation to a user device of the second patient to establish a parent-child contact between the second patient's account and the child account, the second patient being a second guardian of the child.

In some configurations, in response to a request received from the user device of the first patient to remove a parent-child contact with the child account, the processor can be configured to determine whether there is another parent-child contact on the child account.

In some configurations, the processor can be configured to automatically remove the first patient from the child account in response to determining that there is another parent-child contact on the child account.

In some configurations, the processor can be configured to send an alert of the first patient account's access to the child account to the use device of the second patient, wherein the second patient's account has established a parent-child contact with the child account.

The present disclosure provides a secured database system. The system can be configured to receive data related to provider communications in forms of text, audio, and/or video messages. The system can include a processor configured to encrypt the data to output encrypted data and decryption keys upon receiving the data in a first virtual communication room from a first registered user's device when the first registered user is logged into the system on the first registered user's device and has created the first virtual communication room. The system can be configured to allow the first registered user to create additional virtual communication rooms in addition to the first virtual communication room. Each virtual communication room can be created by the first registered user being specific to a particular topic related to the first registered user. The system can include a first server including a first memory device which can be configured to store information of the first virtual communication room including the encrypted data. The first server can be a remote server, and a second server can include a second memory device configured to store the decryption keys. The second server can be a local server. In response to an access request from a second registered user's device received at the first server when the second registered user is logged into the system on the second registered user's device, the first server can be configured to send a request to the second server to retrieve the decryption keys so as to decrypt the encrypted data. The second registered user can be able to view decrypted data on the second registered user's device. The decrypted data may not be stored on the second registered user's device. The data may not be viewable to the second registered user until the second registered user has received and accepted an invitation message from the first registered user to join the first virtual communication room. The second registered user may not have access to the other additional virtual communication rooms created by the first registered user unless the first registered user sends a separate invitation message for any of the additional virtual communication rooms to the second registered user and the second registered user accepts the separate invitation message.

In some aspects, the techniques described herein relate to a system, wherein the first server is a cloud based server.

In some aspects, the techniques described herein relate to a system, wherein the first registered user is a patient.

In some aspects, the techniques described herein relate to a system, wherein the second registered user can invite a third registered user to join the first virtual communication room such that the data is not viewable to the third registered user until the first registered user accepts a request from the third registered user to join the first virtual communication room.

In some aspects, the techniques described herein relate to a system, wherein the second registered user is a physician, and the third registered user is an advanced practitioner such that the advanced practitioner can respond to an inquiry by the first registered user in the virtual room with authorization from the physician.

In some aspects, the techniques described herein relate to a system, wherein the first registered user can authorize the second registered user to receive a notification alert on a mobile device without requiring the second registered user to log into the system, the notification being sent based on a category of a medical condition that is created by the first registered user.

In some aspects, the techniques described herein relate to a system, wherein the processor is configured to force either the first registered user or the second registered user to log out of the virtual communication room after a period of inactivity.

In some aspects, the techniques described herein relate to a system, wherein the period of inactivity is about five minutes.

The present disclosure provides a method of securing database system. The method can comprise the step of including a processor that can be configured to receive data related to provider communications in forms of text, audio, and/or video messages. The method can comprise the step of encrypting the data to output encrypted data and decryption keys upon receiving the data in a first virtual communication room from a first registered user's device when the first registered user is logged into the system on the first registered user's device and has created the first virtual communication room. The method can comprise the step of allowing the first registered user to create additional virtual communication rooms in addition to the first virtual communication room, wherein each virtual communication room can be created by the first registered user being specific to a particular topic related to the first registered user, wherein the system can include a first server including a first memory device which can be configured to store information of the first virtual communication room including the encrypted data, wherein the first server can be a remote server, and a second server can include a second memory device configured to store the decryption keys. The second server can be a local server. The method of securing database system can further comprise the step of configuring the first server to send a request to the second server to retrieve the decryption keys so as to decrypt the encrypted data. The method can comprise the step of enabling the second registered user to view decrypted data on the second registered user's device in response to an access request from a second registered user's device received at the first server when the second registered user is logged into the system on the second registered user's device, wherein the decrypted data may not be stored on the second registered user's device, wherein the data may not be viewable to the second registered user until the second registered user has received and accepted an invitation message from the first registered user to join the first virtual communication room, wherein the second registered user may not have access to the other additional virtual communication rooms created by the first registered user unless the first registered user sends a separate invitation message for any of the additional virtual communication rooms to the second registered user and the second registered user accepts the separate invitation message.

In some aspects, the techniques described herein relate to a method of securing database system wherein the first server is a cloud server.

In some aspects, the techniques described herein relate to method of securing database system, wherein the first registered user is a patient.

In some aspects, the techniques described herein relate to a method of securing database system, wherein the second registered user can invite a third registered user to join the first virtual communication room such that the data is not viewable to the third registered user until the first registered user accepts a request from the third registered user to join the first virtual communication room.

In some aspects, the techniques described herein relate to a method of securing database system, wherein the second registered user is a physician, and the third registered user is an advanced practitioner such that the advanced practitioner can respond to an inquiry by the first registered user in the virtual room with authorization from the physician.

In some aspects, the techniques described herein relate to a method of securing database system, wherein the first registered user can authorize the second registered user to receive a notification alert on a mobile device without requiring the second registered user to log into the system, the notification being sent based on a category of a medical condition that is created by the first registered user.

In some aspects, the techniques described herein relate to a method of securing database system, wherein the processor is configured to force either the first registered user or the second registered user to log out of the virtual communication room after a period of inactivity. In some aspects, the techniques described herein relate to a method of securing database system, wherein the period of inactivity is about five minutes.

BRIEF DESCRIPTION OF THE DRAWINGS

The drawings and the associated descriptions are provided to illustrate embodiments of the disclosure and not to limit the scope of the claims.

FIG. 4 illustrates a patient add issue screen on a user interface or a portion thereof.

FIGS. 5A-5B illustrate an example patient profile health chart on a user interface or a portion thereof.

FIG. 6 illustrates an example patient profile documents vault on a user interface or a portion thereof.

FIG. 9 illustrates example patient contacts provider permission settings on a user interface or a portion thereof.

FIG. 11B illustrates an example patient contacts invitation queue on a user interface or a portion thereof.

FIG. 14 illustrates an example provider view of the patient health chart on a user interface or a portion thereof.

DETAILED DESCRIPTION

Figure 1:
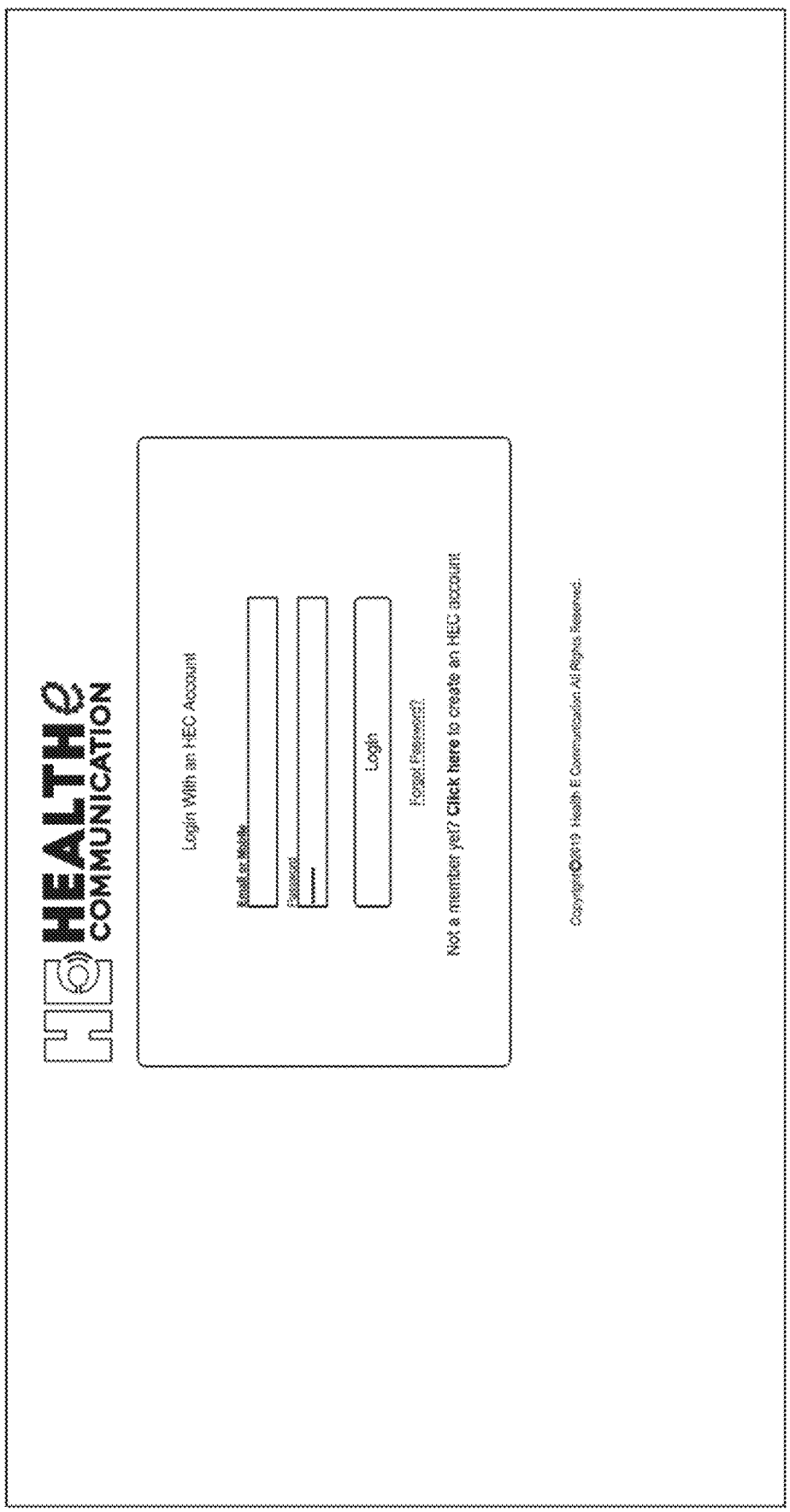
FIG. 1 illustrates an example login screen on a user interface or a portion thereof.

There are advantages in providing a platform for various parties of a healthcare applications, such as to more effectively and securely communicate regarding a patient's health issues and thereby providing improved patient care. U.S. Patent Application Publication No. 2011/0046976A1 (the '976 application), entitled "Integrated Communications System," the entirety of which is incorporated herein by reference and should be considered a part of the specification, describes an example integrated communication system providing such a platform.

FIGS. 1-16 illustrate example user interfaces of an example system that facilitates communication among patients, healthcare providers, consultants, family and friends, caregivers, surrogates, and/or others. The system can have any features of the system described in the '976 application. Optionally, the system allows for asynchronous and/or real time access by the various parties so that all the interested parties can be effectively updated on an issue of a patient. The interested parties can include the patient, a main healthcare provider to the patient, consultant(s) invited by the main provider (such as a specialty physician, therapist, or others), the patient's family, friends, caregiver(s), and/or surrogates.

The system disclosed herein can provide certain advantages and/or solve certain problems in patient care. The system can streamline the patient care process, reducing wasteful and/or ineffective care pathways, such as avoidable visits to the doctors' offices and/or the emergency room. The system can be widely adopted as telehealth or telemedicine is becoming mainstream and an integrated mode of treatment in many states in the United States. The system can reduce communication gaps and frustration resulted therefrom, and/or improve effective communication and care coordination, such as among the healthcare professional, the patients, and the patients' family and friends. For example, the patient's issue and related discussion with the doctor, next-of-kin, and/or caregiver, etc. only need to be posted once in the system for any of the interested parties to be informed and updated.

Asynchronous access by the members of the communication system does not require any of the communicating members to be signed into the system and having joined a discussion thread or online meeting at the same time. For example, as will be described in more detail below, a patient can login to the patient's account to leave a question for a healthcare provider. The healthcare provider needs not be signed in to the system when the patient leaves the question. The healthcare provider can review the patient's question at a different time, and the patient needs not be signed in to the system when the healthcare provider answers the patient's question. The patient may also have included a family member in the discussion with the healthcare provider. The family member may be offline when the patient leaves the question, and may view and optionally respond to the patient's question at a later time. The asynchronous access makes it easier to keep every interested party on the same page regarding a patient's health issue without requiring all the interested party to be present for a discussion of the issue (such as at the doctor's office or in an online meeting format), which may be difficult to schedule and cause delay in addressing the patient's health issue. The asynchronous access also reduces miscommunication and/or repetitive communication about the same issue due to one or more of the interested parties not being present at the discussion.

From a healthcare provider (for example, a clinician)'s perspective, the system disclosed herein can allow the provider to create secure, optionally asynchronous virtual interactions. As a result, the system can reduce and/or eliminate unnecessary office visits, such as a revisit of a patient accompanied by a family member who was not present at an initial visit of the patients. The provider can reduce the amount of time spent on email and/or text message communications with patients and/or their family or friends. The provider can have more time for more important face-to-face interactions. Using the system, the provider can also more easily include consultants and/or other providers when needed, such as when experts from a different field are needed for the patient's health issues and/or when the provider is unavailable to care for the patient. The provider can also include a patient's caregiver(s), family, and/or friends in the communication than in a traditional face-to-face setting to more efficiently involve one or more of the patient's caregiver(s), family, and/or friends in important care functions, such as by communicating with one or more of the patient's caregiver(s), family, and/or friends to provide instructions on how to care for the patient and/or receive feedback from the patient's caregiver(s), family, and/or friends.

The system and/or processor of the present disclosure can allow the users to create virtual rooms and/or certain topics where the patient can share their health data with their healthcare provider and other people (e.g., family member(s), friend(s), physician(s), advanced practitioner(s), surrogate(s)). Each virtual room can enable physicians, with the permission of the patient, to engage other healthcare providers (e.g., other physicians, nurses, advanced practitioners, etc.) for a certain topic or medical issue. As will be described in more details elsewhere in the present disclosure, physicians or other healthcare providers who are invited by the patient to one virtual room will not have access to other virtual rooms by the patient unless the patient has invited them to those other virtual rooms. For example, a physician can recommend and/or invite a specialist to access a virtual room that corresponds to a particular medical issue that is beyond the physician's area of expertise with the permission of the patient, and/or the physician can recommend and/or invite an advanced practitioner to a virtual room (again with the permission of the patient) so that the advanced practitioner can monitor the virtual room, respond to certain inquiries (with the physician's permission) and attend to any emergency matter when the physician may not be available. The patient can grant limited or complete access to information in the virtual room to a newly added provider (e.g., the specialist, the advanced practitioner, etc.). A complete access can allow the invited specialist to see all conversations and documents between the patient and the physician with respect to a particular medical issue that is the subject of that virtual room. In some aspects, the physician and/or the patient can specify the duration in which the newly invited healthcare provider can access a particular virtual room. Once that duration is over, the newly invited healthcare provider can lose access to the virtual room and the level of access can be returned to prior the invitation. For example, the system can allow for both the original physician and the covering healthcare provider to have access to medical data during this period. This can allow the original physician to continue to monitor the communications between the patient and the newly assigned healthcare provider.

The system described in the present disclosure can allow for a more secure and accurate data transfer between different healthcare providers. This can provide an advantage over traditional ways of communicating a patient's health information where the physician may send a patient's health data via unsecured email, unsecured attachment to emails, and/or communicate it with word of mouth to a covering healthcare provider. Similarly, in the traditional ways of communication, once the covering healthcare provider completes the coverage, he/she may use a same or similar unsecured way to communicate the patient's healthcare data back to the original physician. These traditional ways of communication among physicians, particularly those who do not have access to the same Electronic Medical Record (EMR) system, are less secure and/or more prone to inaccuracy. With the advantages provided in the present disclosure, once a physician invites another healthcare provider to a virtual room (and the patient grants access), the newly invited healthcare provider, can securely access the patient's health information regardless of whether the covering provider is from the same or a different Electronic Medical Record (EMR) system. Similarly, the primary or original physician will have secured access to the documentation by the covering provider of the patient's health information, which is more contemporaneous and therefore more accuracy and/or complete. The primary or original physician has the option of viewing the documentation while the covering provider is still providing coverage or later after the coverage has ended.

The system described in the present disclosure can allow physicians to have a quick and easy access to certain information while requiring the physician to go through a more secured process to access other information about the same patient. For example, the patient can tailor the privacy and/or security level of a particular virtual room (or topic) such that once the virtual room is created, the healthcare provider can receive an instant notification of the patient's discomfort (e.g., mild, moderate, severe) in an email or text message or the like. The healthcare provider can then access the virtual room through the secured process of the present disclosure to see the details of the discomfort and attend to the patient's need accordingly.

From a patient and/or the patient's caregiver's perspective, the system can allow more effective sharing of information about the patient among the patient's provider, caregiver, family, and/or friends. The caregivers can be more actively involved in learning how to care for the patient without having to be physically present at every consultation with the provider. The patient and/or caregivers can have asynchronous and/or real-time access to care by the provider with reduced hassle of scheduling and/or waiting outside a doctor's office. The patient and/or caregivers can also track information related to the patient's care in an easier and more accessible fashion than having to request records from the doctor's office.

The system can also help patients share their health data in a more secured and private manner. Each virtual room can be specific to one medical issue or topic, and the users can create more than one virtual room to address different issues that the patient may have. This can enable the patient to set up different communication groups for different medical issues and/or choose who can access different health/medical data. The patient can also provide a blanket access to certain individual(s). For example, the patient can grant access to a caregiver (for example, the patient's next of kin, etc.) such that the caregiver can access all virtual rooms and/or discussion topics without a need to request access to individual virtual rooms. The system can also allow the patient to disallow access to certain information in a virtual room or access to certain virtual rooms to someone who has been granted a blanket access. Only people who have been granted access by the patient can access the medical data and conversations that take place within a particular virtual room.

The system and/or processes described in the present disclosure can allow the patient to communicate with their healthcare provider in a more efficient manner and reduce (or eliminate) the voluminous communications between the patient and the healthcare provider that occurs in traditional systems. The patients can input their medical conditions (or their general inquiry) in different categories that can be sorted and/or filtered on the healthcare provider's end. For example, different categories can include the level of discomfort (which can allow the healthcare provider to judge the urgency of the matter), whether the inquiry relates to a recurring condition, or whether the inquiry relates to another existing inquiry between the patient and the healthcare provider. This can allow the patients to communicate their needs more effectively with their healthcare provider without worrying about the volume of information that is communicated. The sorting and filtering can also allow the physician to better prioritize the responses to the patient's messages.

Figure 22:
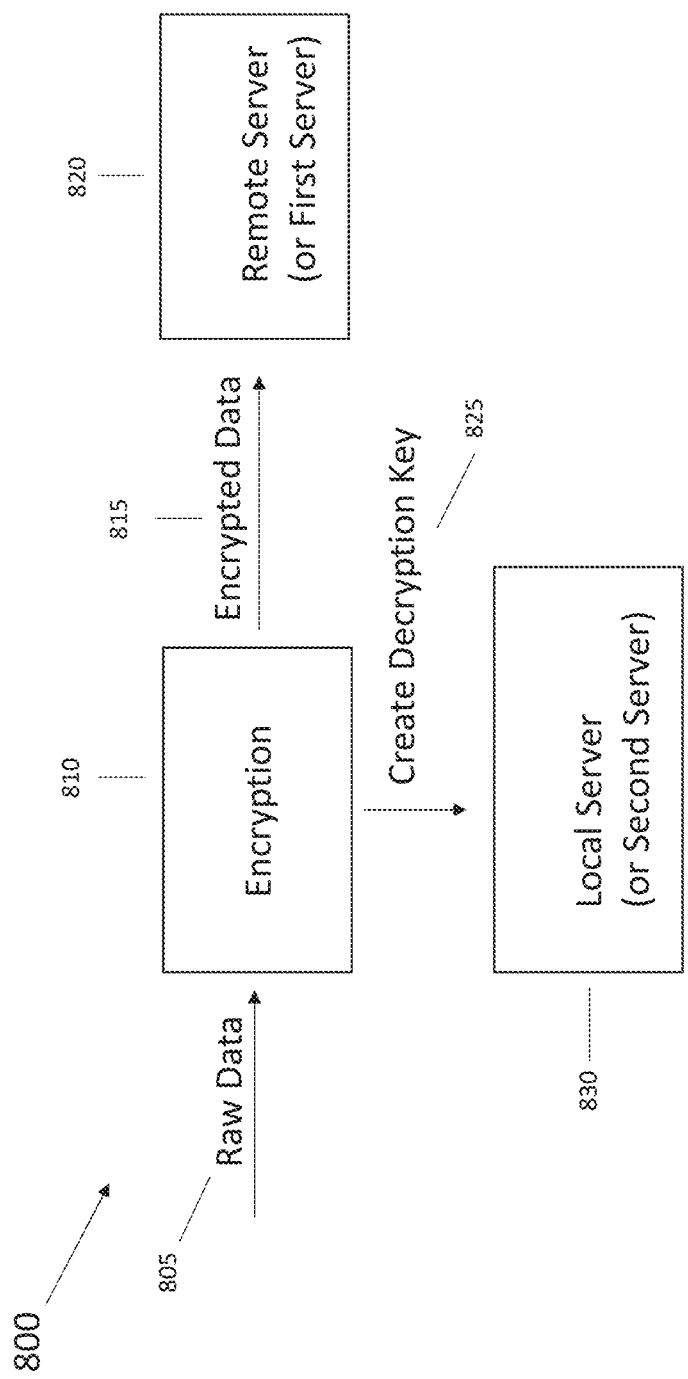
FIG. 22 illustrates an example encryption block diagram according to one aspect of the present disclosure.
Figure 23:
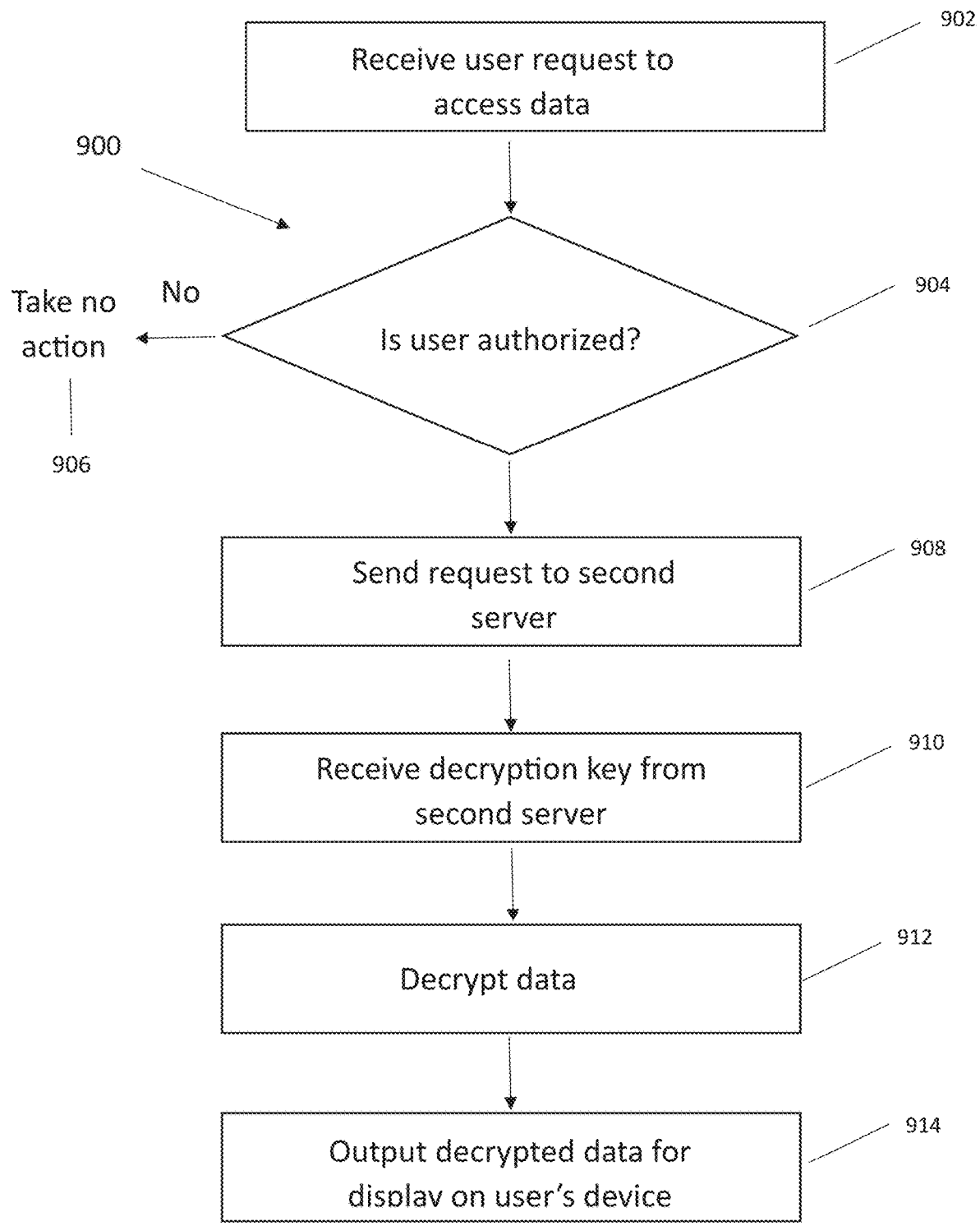
FIG. 23 illustrates an example decryption process according to one aspect of the present disclosure.
Figure 24:
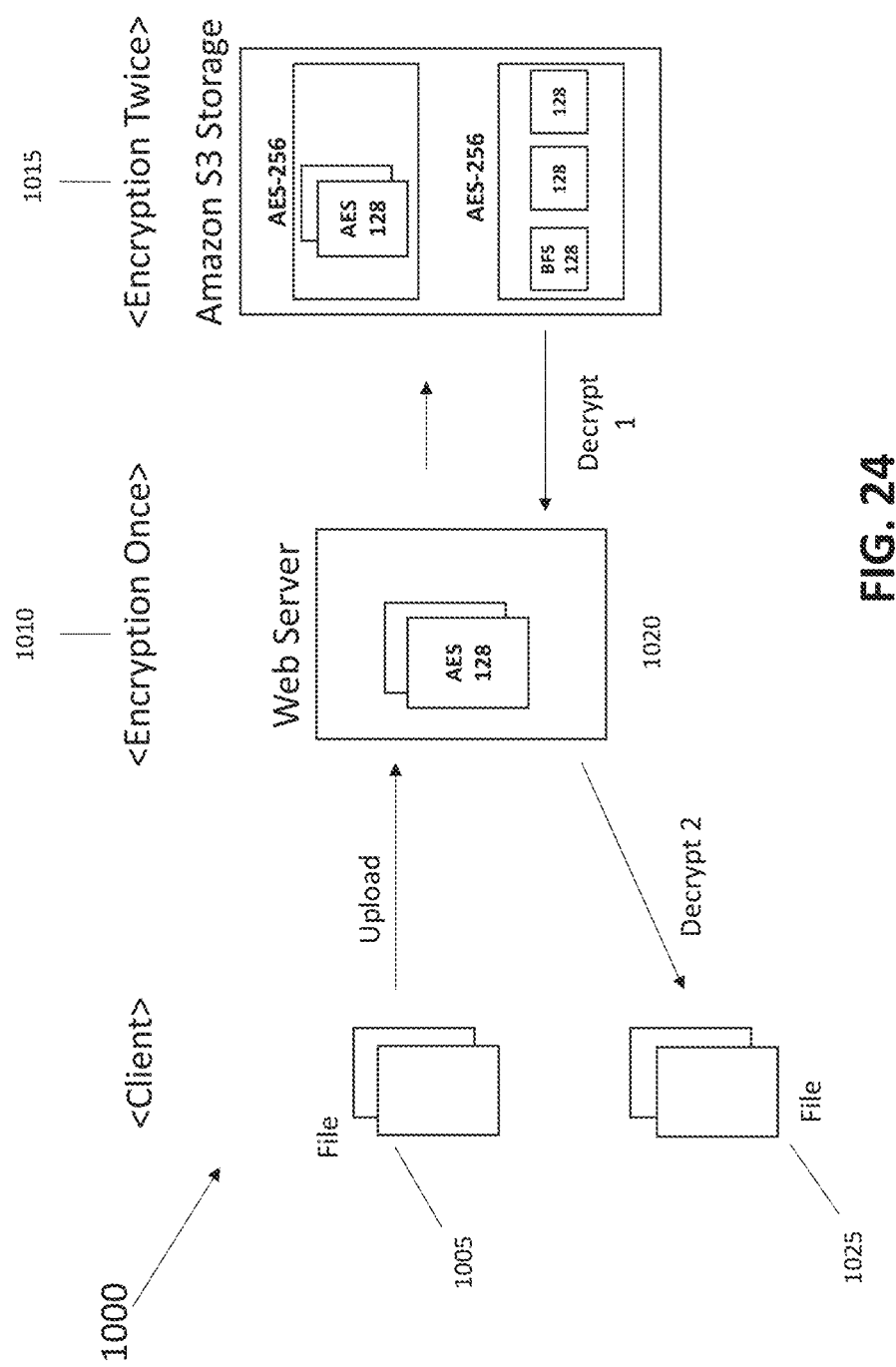
FIG. 24 illustrates another example encryption and decryption system according to another aspect of the present disclosure.

As shown in at least FIGS. 22-24, the system and/or processes described in the present disclosure can provide a secured mechanism for users to share data with other users. The data that users can share amongst each other can be in different formats, for example, text, media, picture, audio, video, or any combinations thereof. As it can be seen in FIG. 22 with respect to a process 800, once the raw data is uploaded into the platform of the present disclosure at step 805, a processor of the system at step 810, for example, a backend controller of the system, can add encryption to the received data to make it unreadable for an unauthorized user. In some embodiments, the processor can manipulate existing codes suitable for receiving the data from the patient at step 815 to enhance security. Such existing codes are available for processing multimedia data, which are used by many social media sites for processing user-provided content. However, such existing codes may lack the level of security required for handling healthcare related information. In some embodiments, the processor can encrypt the said data and upload the encrypted data in a first server at step 820. Similarly, once the raw data is uploaded into the platform at step 805, the processor of the system at step 810 can create a decryption key at step 825 and upload the decryption key in a second server that is different from the first server at step 830.

The encrypted data can provide enhanced security by making the data unreadable to an unauthorized user. For example, an unauthorized user may obtain access to the first server where the patient's data is stored. However, the unauthorized user may not be able to read or decipher the encrypted information without access to the decryption key, which is stored in the second server. In some aspects, the first server can be a commercially available cloud server such as Amazon Web Service (AWS). In some aspects, the second server can be another remote server or a local server.

As it can be seen with respect to a decryption process 900 illustrated in FIG. 23, a local server can be configured to require a user to enter a user and password and/or receive an access request at step 902 to access the data stored in the first server. If the user is not an authorized user, the processor takes no action at step 906 (or output a message that the user is not authorized), and the user cannot access the encrypted data. If, at step 904, the user is an authorized user, the first server can send a request to a second server at step 908. The first server can receive the decryption key from the second server at step 910 and decrypt the information uploaded in the first server at step 912. The first server can make the information readable for the user at step 914. In some other embodiments, the second server can be another commercially available server such as Amazon AWS S3 storage. The system can implement further mechanisms to enhance the security of the platform. For example, the first and/or the second server can use commercially available products such as Identity and Access Management (IAM) provided by Amazon AWS to control the authentication and access to the servers. All information and data in the processor can be configured to securely reside on the server so that no data is sent and/or stored in a user's device. This can allow a user to utilize any device without having to worry about sensitive information being stored in a local device.

With continued emphasis on the security features of the present disclosure, FIG. 24 illustrates yet another example process 1000 of encryption and decryption of raw data once a user uploads their data into a webserver. At step 1010, the processor can perform a first level of encrypting the raw data. In some embodiments, the first level of encryption can be performed via commercially available products such as Advanced Encryption Standard (AES) algorithms with 128-bit keys on the webserver, or any other suitable encryption product. A second level of encryption can be performed on the data encrypted with 128-bit keys at block 1015. In some embodiments, the second level of encryption can be performed via commercially available products such as AES algorithms with 256-bit keys on a commercially available server such as Amazon S3 storage, or any other suitable cloud based servers. Similarly, upon initiating a decryption request, the twice encrypted data in block 1015 can be decrypted back to the web server at step 1020 and be converted to decrypted file at step 1025. In some embodiments, the decryption key can be stored in the commercially available Amazon S3 storage. In some other embodiments, as discussed with respect to FIG. 21 and in other parts of this application, the decryption key can be stored in a local server. From the perspective of hospitals and/or other healthcare institutions, the system can reduce readmission rates related to poor communication and lack of follow-up between the provider and the patient (and/or the patient's caregiver, family, and/or friends). The system can reduce waste in healthcare facilities, such as surgical facilities, due to poor pre-op preparation as a result of poor communication to the patient (and/or the patient's caregiver, family, and/or friends). The system can also ensure in-person communication events to be more likely clinically necessary visits, thereby increasing the amount of medical resources for patients who need care. These improvements can improve patient satisfaction and compliance with regulation. Moreover, the asynchronous communication can allow more effective communication needed for better patient care delivery. The system can also facilitate a team-orientated approach to communication with the patient (and/or the patient's caregiver, family, and/or friends) and care coordination.

The virtual rooms of the present disclosure can allow hospitals to better allocate their resources. For example, hospitals can allocate more resources to attend to more urgent matters based on the category of input by the patient. The system can also allow hospitals to discourage patients from submitting unnecessary inquiries. For example, the hospitals and/or healthcare institutions can charge patients per inquiry or per each virtual room or topic that the patient creates. The system and processor of the present disclosure can allow a patient to own their data and delete virtual rooms, topics, or medical records that are erroneous, old, obsolete, etc., and thus allow the user to maintain a more accurate data base of their medical history.

The system disclosed herein can provide a secured platform for patients and healthcare providers to share medical data. The system can be configured so that only users with invitation can create an online account (and obtain login information) to access the platform. The system can be configured so that a user can only access the platform from one device. For example, the system can detect that a certain username/password is entered in more than one device and consequently force the user to log out from all other devices. The system can also be configured to force the user to log out of the platform if there is a period of inactivity. For example, the system can force the user to logout after an idle period of about 5 minutes, or about 6 minutes, or about 7 minutes, or any other value smaller than about 5 minutes or larger than about 7 minutes or between about 5 minutes to about 7 minutes, depending on the user's security needs. The system can also force the user to logout after the user stays logged in the platform for a long period, the duration of which can be adjusted based on the user's need.

Figure 2:
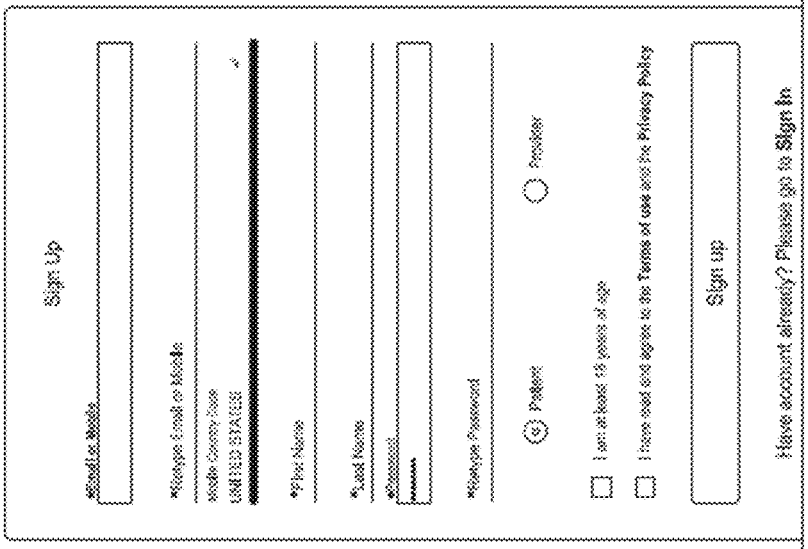
FIG. 2 illustrates an example registration screen on a user interface or a portion thereof.

As noted above, the web-based communication system disclosed herein is a secured system. For example, as shown in FIGS. 1 and 2, the system requires a user to be registered as a member, which includes creating a password-protected account. A registered member can securely login with a password. Optionally, the system can offer a two-step authentication step, such as sending a temporary code to the member's registered mobile phone, sending a secure link to the member's registered email address, scanning the member's fingerprint, using facial recognition, retina recognition, or otherwise. As shown in FIG. 2, the account created can be for a patient or a healthcare provider. Optionally, a user can only sign up for an account upon receiving an invitation, for example, from a patient, a provider, and/or a healthcare institution.

Figure 3:
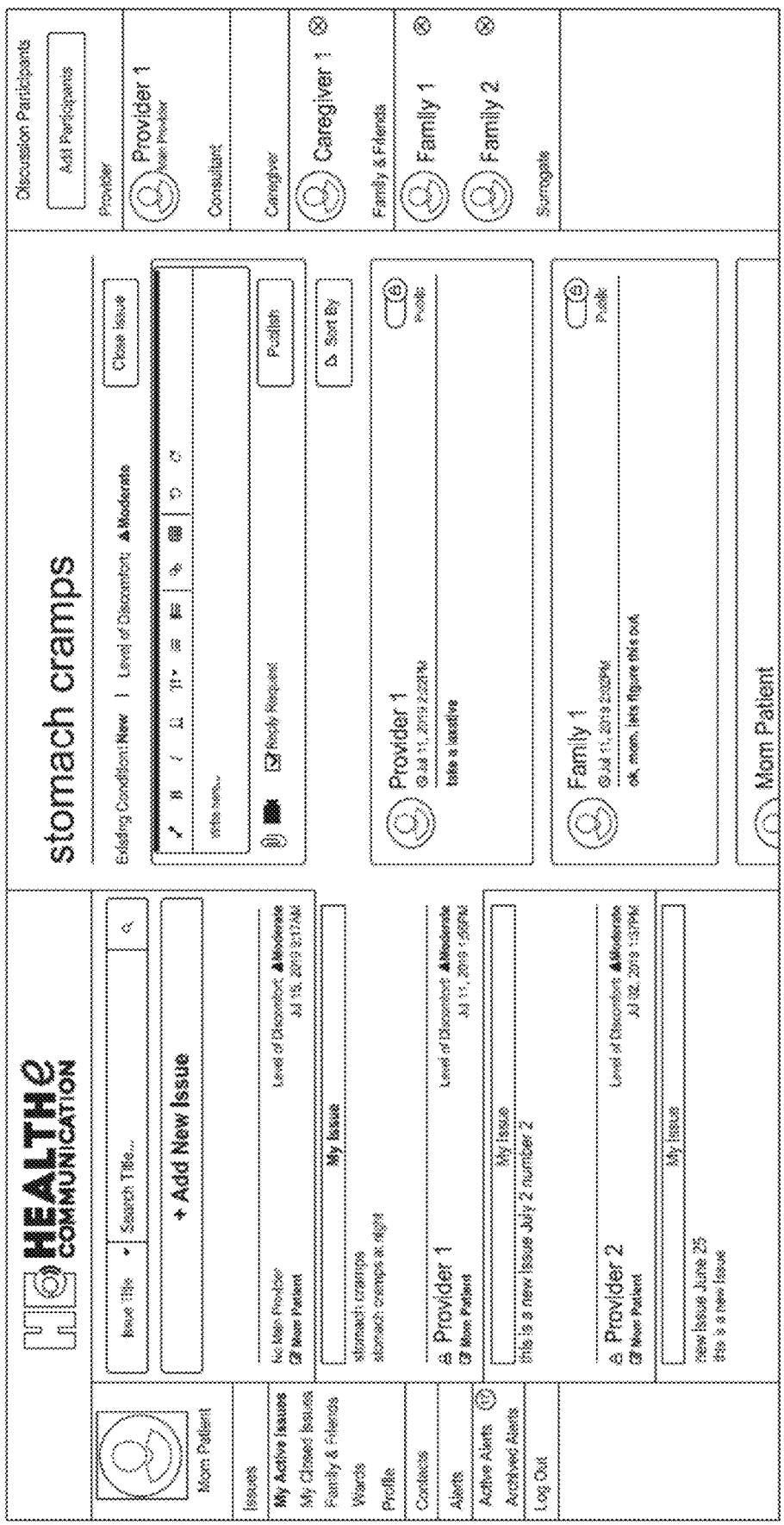
FIG. 3 illustrates an example patient main issue screen on a user interface or a portion thereof.
Figure 4:
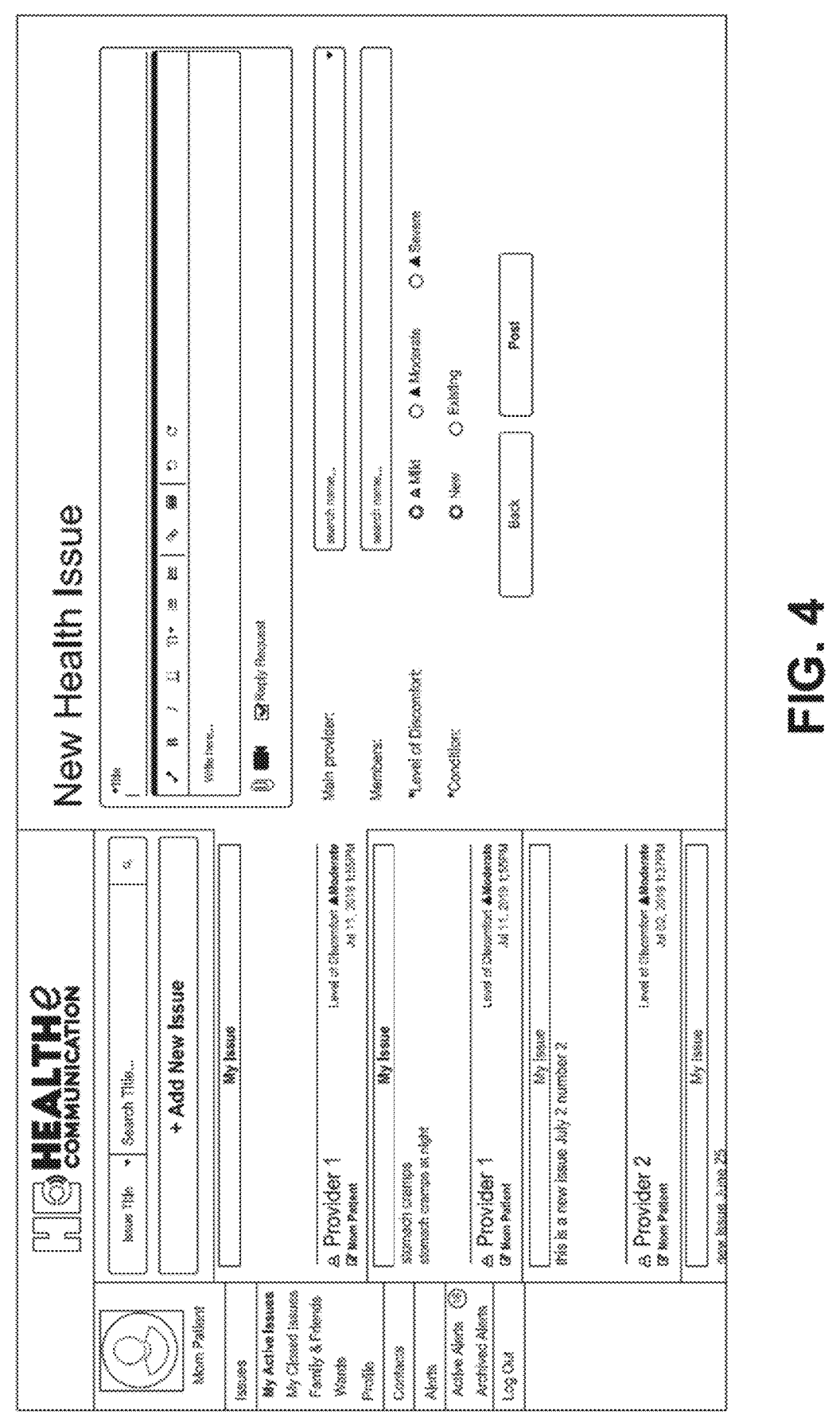

FIGS. 3-12 illustrate example user interface displays of the system when the member is a patient. As shown in FIG. 3, the patient can view the patient's active health issues. The active issue entry can be created by the patient, such as shown in FIG. 4. The patient can select one or more providers with whom to share the entry. The patient may select different providers for different health issues. A provider can only view the issue shared by the patient with that provider. Optionally, the patient can rate the level of discomfort, such as "mild," "moderate," and "severe," or alternatively on a scale of 1-5 or 1-10, or otherwise. The level of discomfort indicated by the patient can help the provider prioritize the provider's resources. Optionally, the patient can identify whether the condition is new, existing, and/or recurring. As shown in FIG. 4, the patient can have the options of uploading photos and/or video related to the issue. The patient can upload images locally onto one device so that the images get transferred to the server of the system. Additionally or alternatively, the patient can directly upload the images to the server. The provider can view the issue reported by the patient asynchronously so that the patient can avoid lengthy waiting time at the provider's office or the hassle of scheduling an appointment with the provider.

With continued reference to FIG. 3, the patient can optionally invite the patient's caregiver, family and/or friends, and/or surrogate to participate in the discussion of the issue. Optionally, the provider can have the authorization from the patient to invite additional parties. The communications can be permission-based. Each invitation of a party to the conversation can be permitted by the patient. For example, the consultant can be invited by the main provider based on the issues described by the patient, but needs to be approved by the patient. Each invited party can choose to accept or decline the invitation. Each communication can be designated as public or private by the patient so that the patient can customize which invited parties can view the particular communication. As also shown in FIG. 3, once an active issue has been resolved, the patient can close that issue, which can be archived under a tab "My Closed Issues." The system can allow the patient to customize the permission for other users to view the closed issues.

Figure 5A:
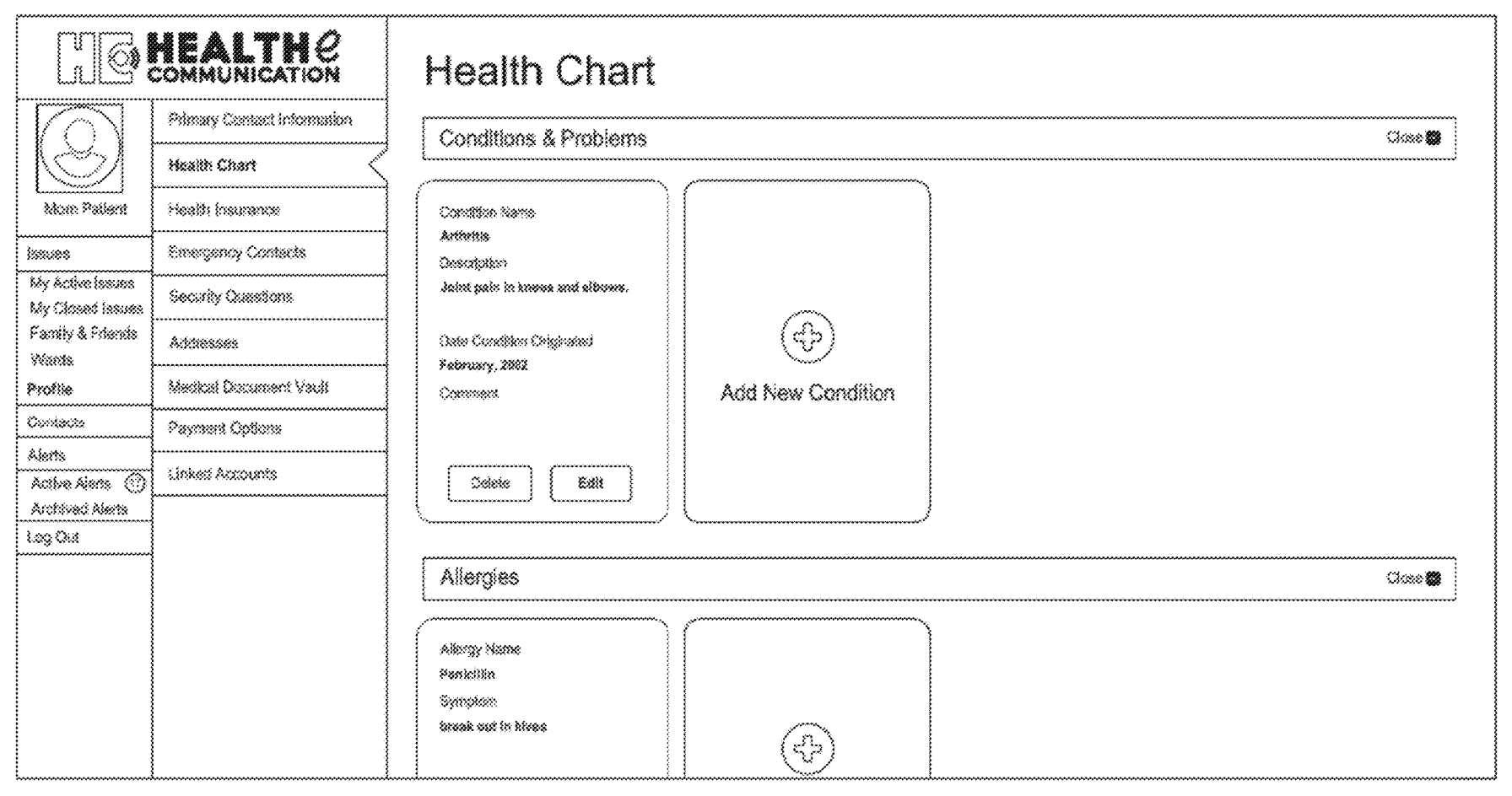
Figure 5B:
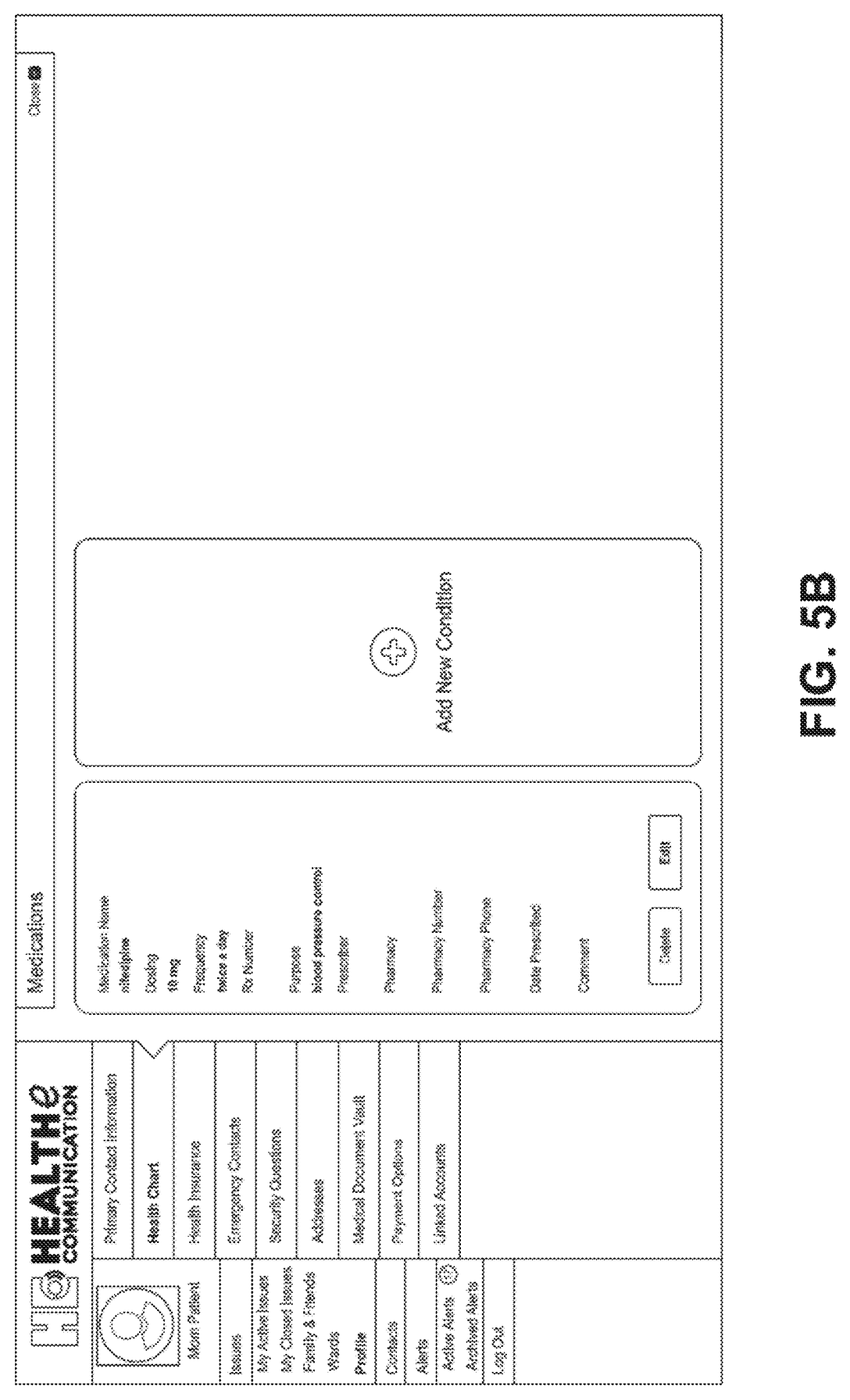
Figure 6:
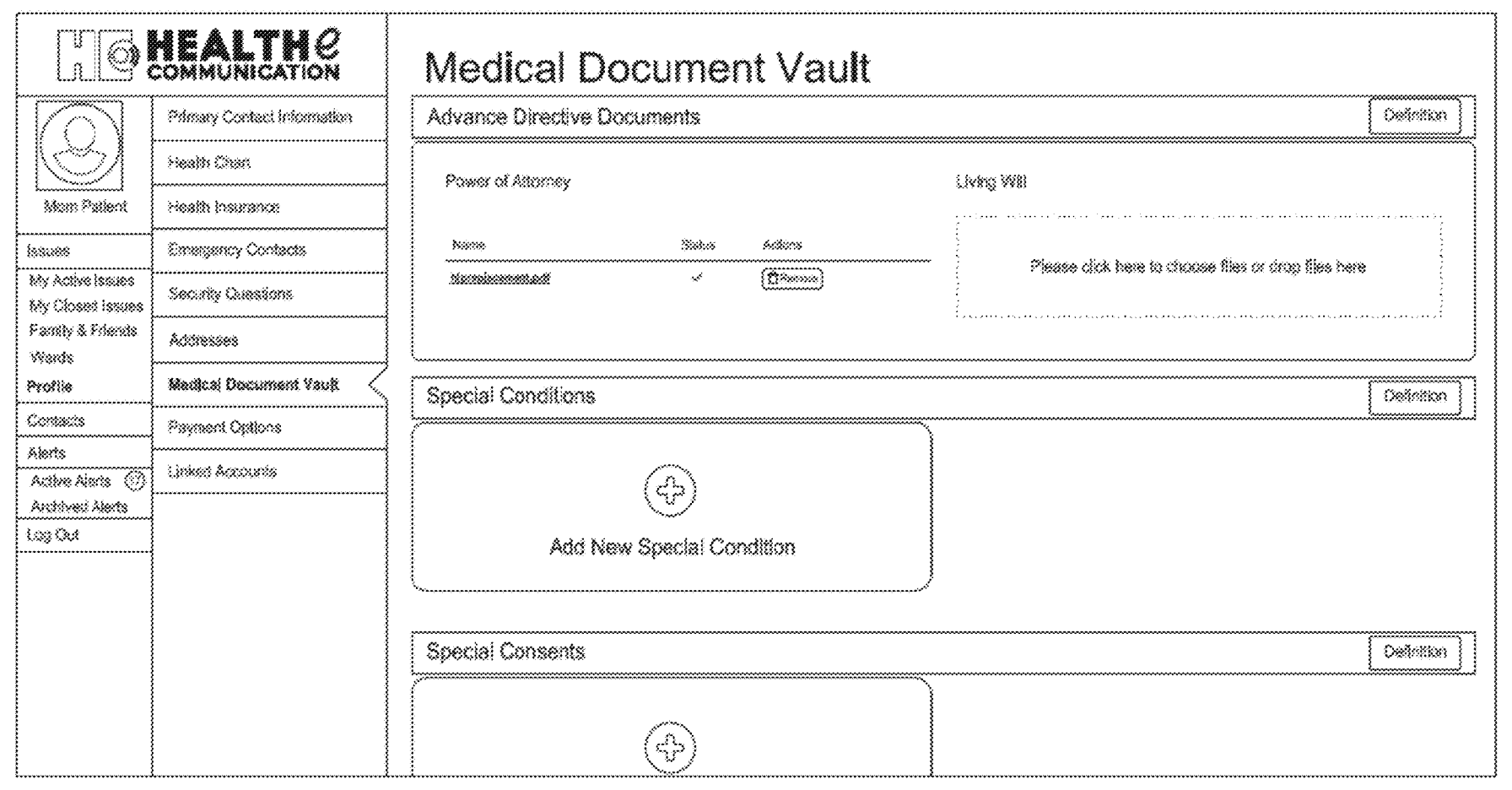
Figure 7:
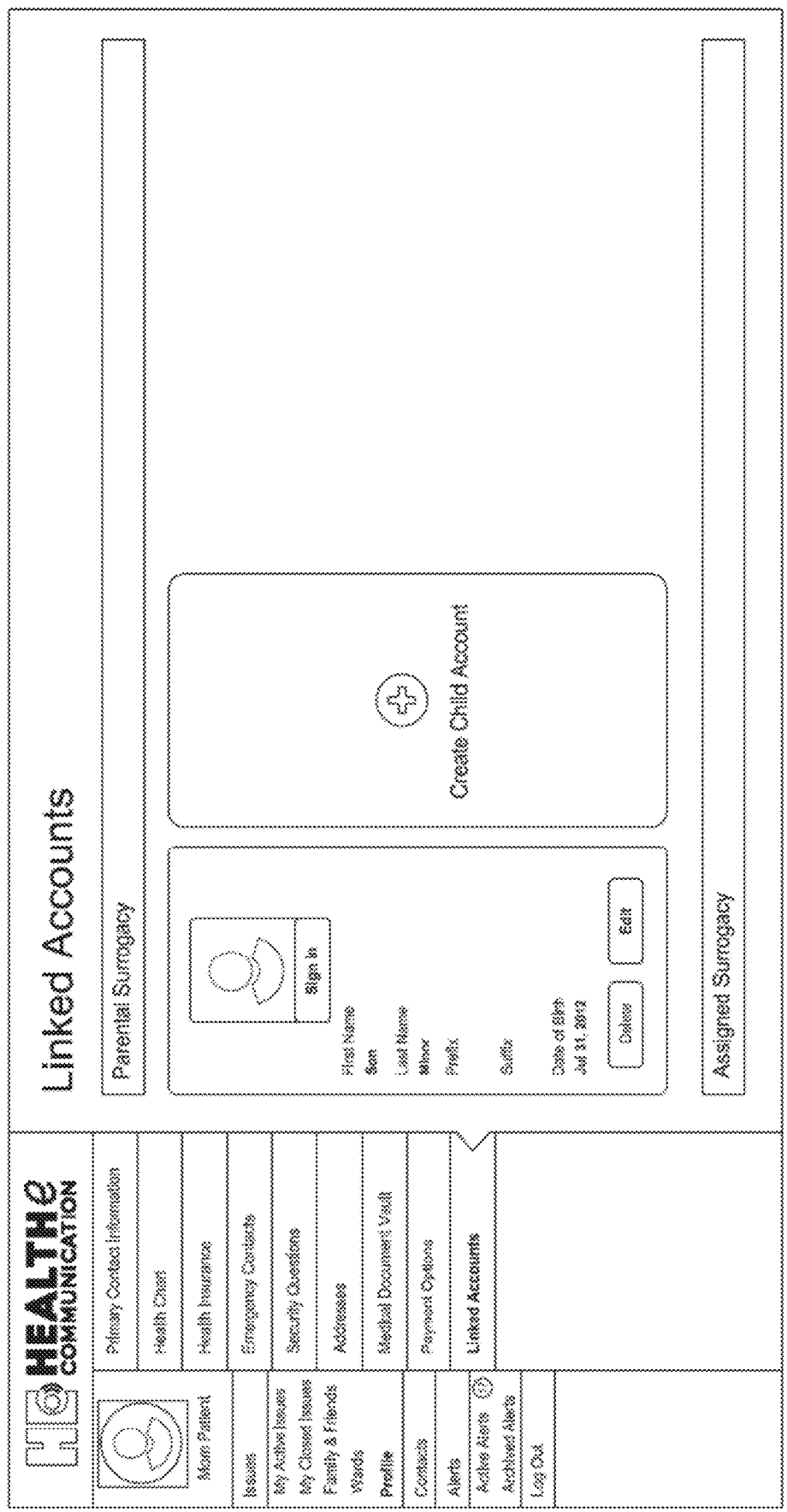
FIG. 7 illustrates example patient profile linked accounts information on a user interface or a portion thereof.

As shown in FIGS. 5A-7, the patient is able to view the patient's profile after the secured login. The profile tab can be expanded into a plurality of subtabs, such as "Primary Contact Information," "Health Chart," "Health Insurance," etc. The list shown in FIGS. 5A-7 are for illustrative purposes and is not exhaustive. FIGS. 5A and 5B illustrate the Health Chart subtab. The Health Chart can include a collection of the patient's health history, such as past and/or current health conditions and/or problems, any allergies, medication prescriptions, past surgeries, health check-up records, immunization records, and/or the like. FIG. 6 illustrates a Medical Document Vault subtab. The medical document vault can store legal documents for the patient, such as a power of attorney, a living will, consent forms, special conditions, and/or the like. FIG. 7 illustrates a Linked Accounts subtab. The patient may have minor children and/or elderly parents, for whom the patient serves as a surrogate. The minor children and/or elderly parents' accounts, and/or other members' accounts, such as when the patient acts as a surrogate for friends, siblings, etc., can be accessed from the Linked Accounts subtab. Optionally, separate login information can be required to access the linked accounts. The Linked Accounts subtab can also include account(s) of a party who can serve as the patient's chosen or assigned surrogate.

Figure 8:
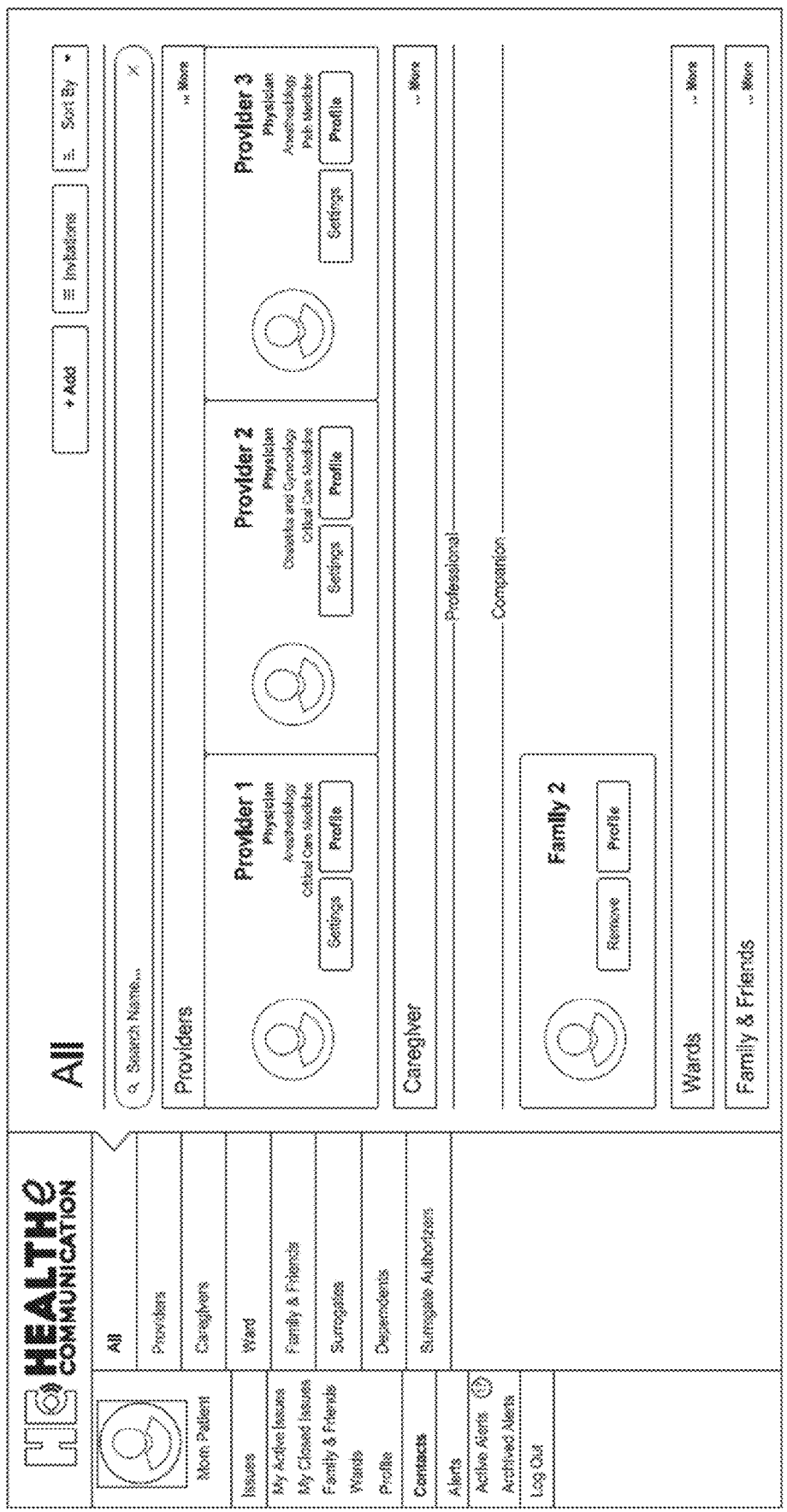
FIG. 8 illustrates an example patient profile contact list on a user interface or a portion thereof.
Figure 9:
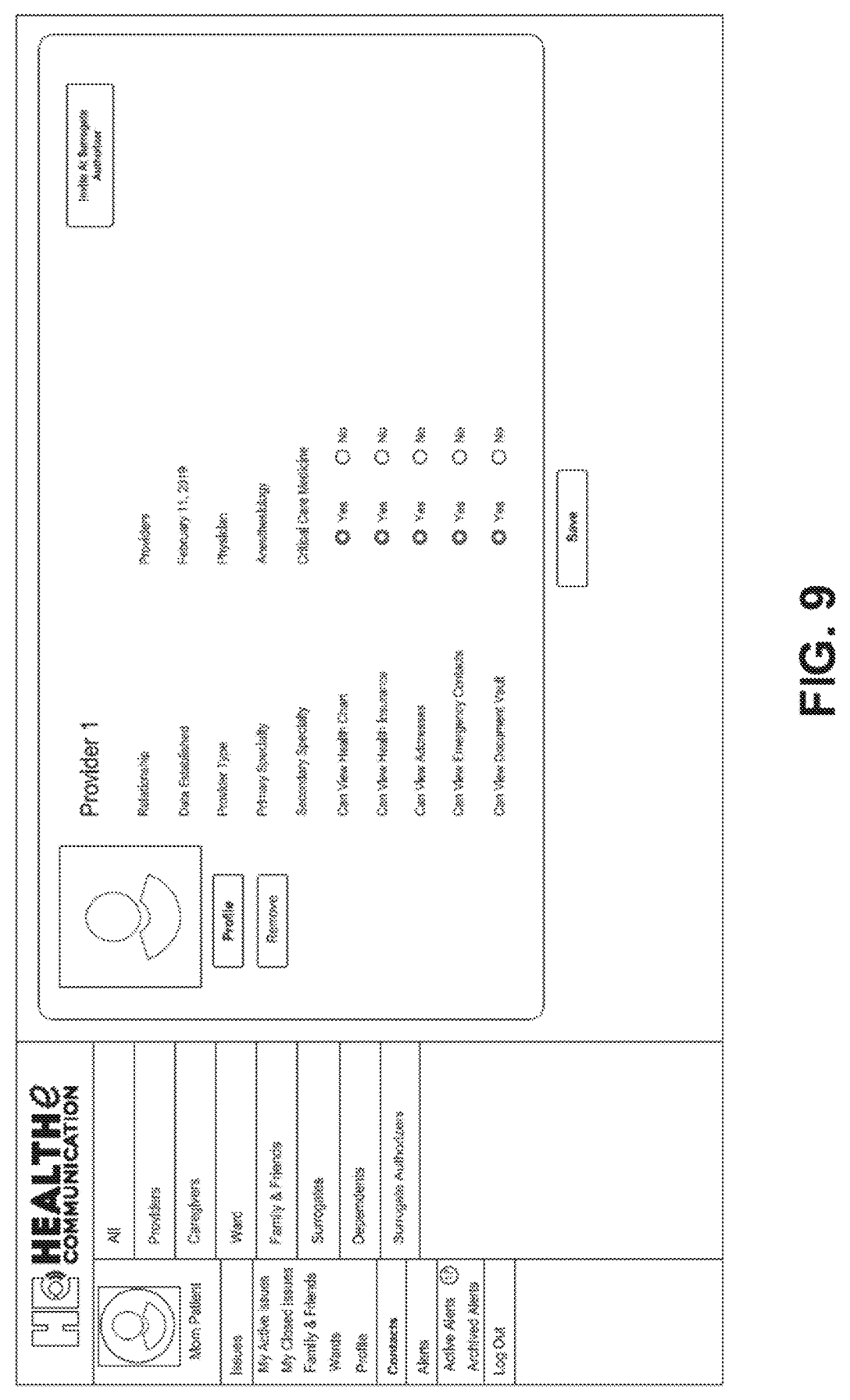
Figure 10:
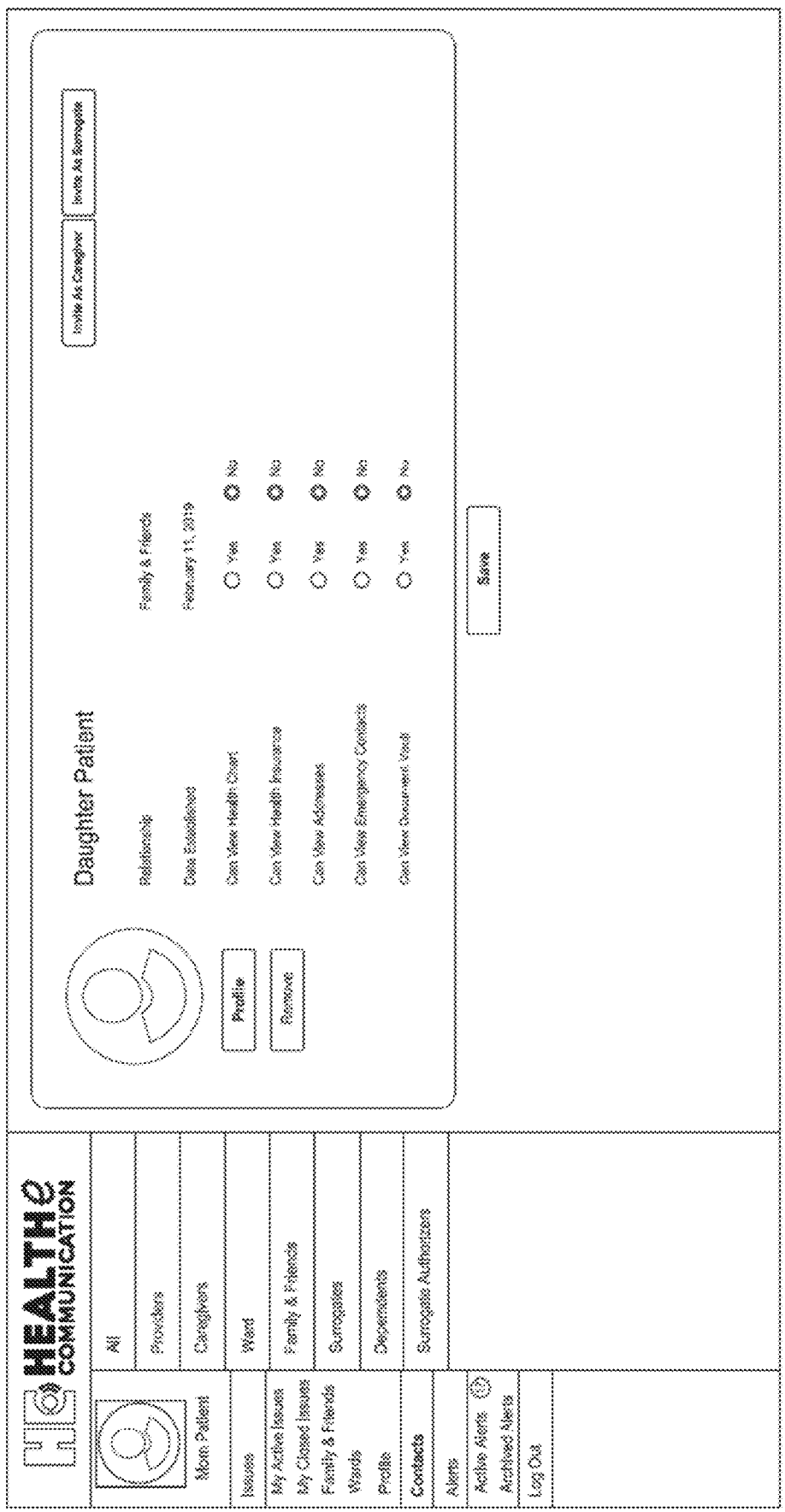
FIG. 10 illustrates example patient contacts family and friends permission settings on a user interface or a portion thereof.
Figure 11A:
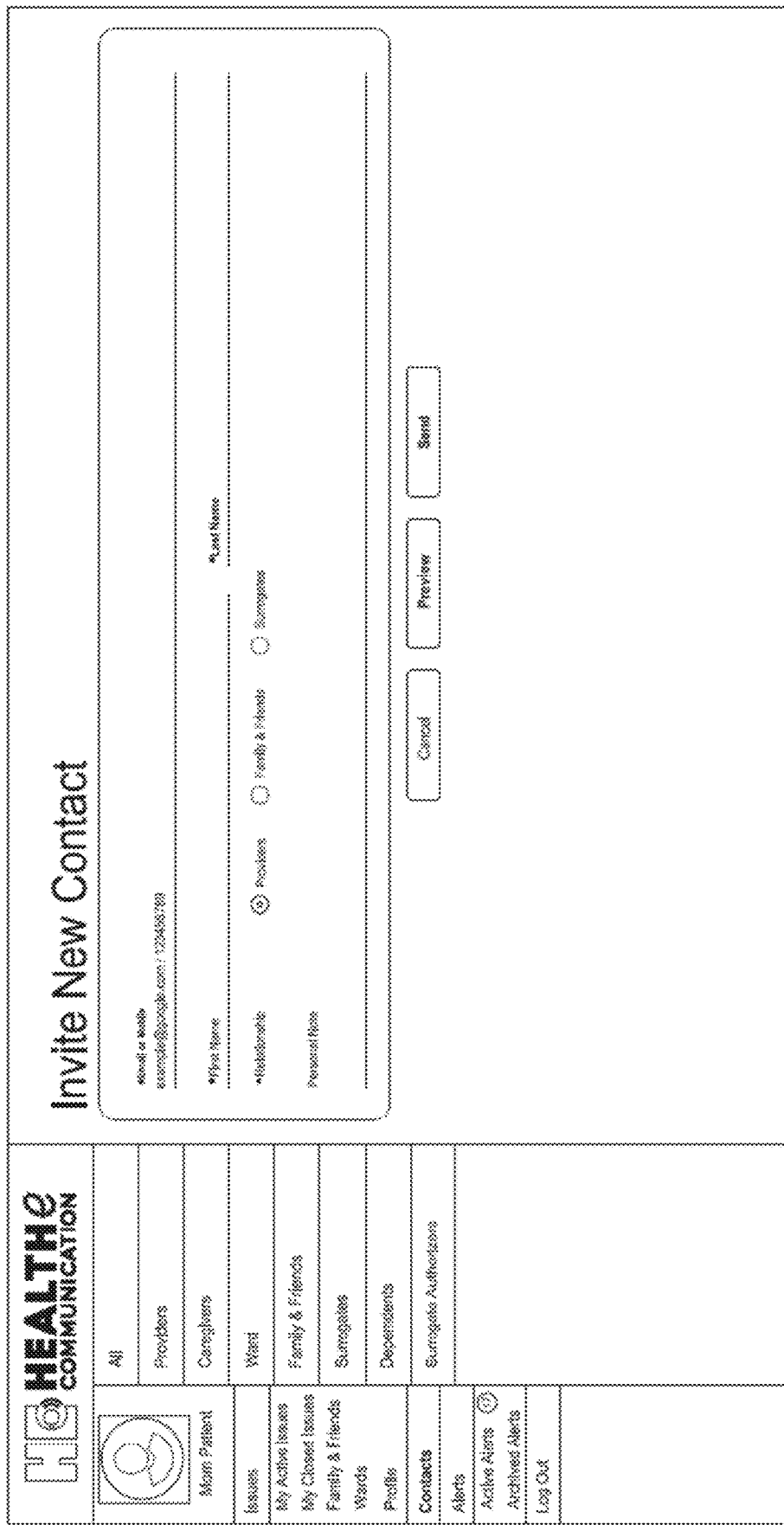
FIG. 11A illustrates an example patient contacts invite new contact screen on a user interface or a portion thereof.

In addition to the linked accounts, the patient may be connected to one or more contacts, including but not limited to providers, caregiver(s), ward, family, and/or friends. The contacts can be accessed by clicking on the "Contacts" tab on the user interface, such as shown in FIG. 8. The contacts can be categorized based on the roles of the contacts, such as Providers, Caregiver, Wards, and Family and Friends, Surrogates, or otherwise. As shown in FIGS. 9 and 10, the patient can customize the level of access and/or control of each contact, such as by restricting views on certain information under the patient's account in the system. For example, the patient may provide more access to the provider than to a family member or friends. As shown in FIGS. 11A and 11B, the patient can invite new contacts and view a list of the sent contact invitations and the status of those invitations. The patient can also view a list of received contact invitations by other members or users of the system.

Figure 12:
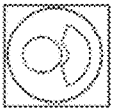
FIG. 12 illustrates an example patient contacts new issue invitation alert on a user interface or a portion thereof.

As shown in FIG. 12, the patient can be alerted of updates and notifications in the system related to the patient. For example, the patient can be notified when a participant of an active issue of the patient posted a new message, and/or when an invitation has been accepted and/or declined. The patient can accept or decline the new messages received. Only the accepted messages may be stored as part of the record for the active issue.

Figure 13:
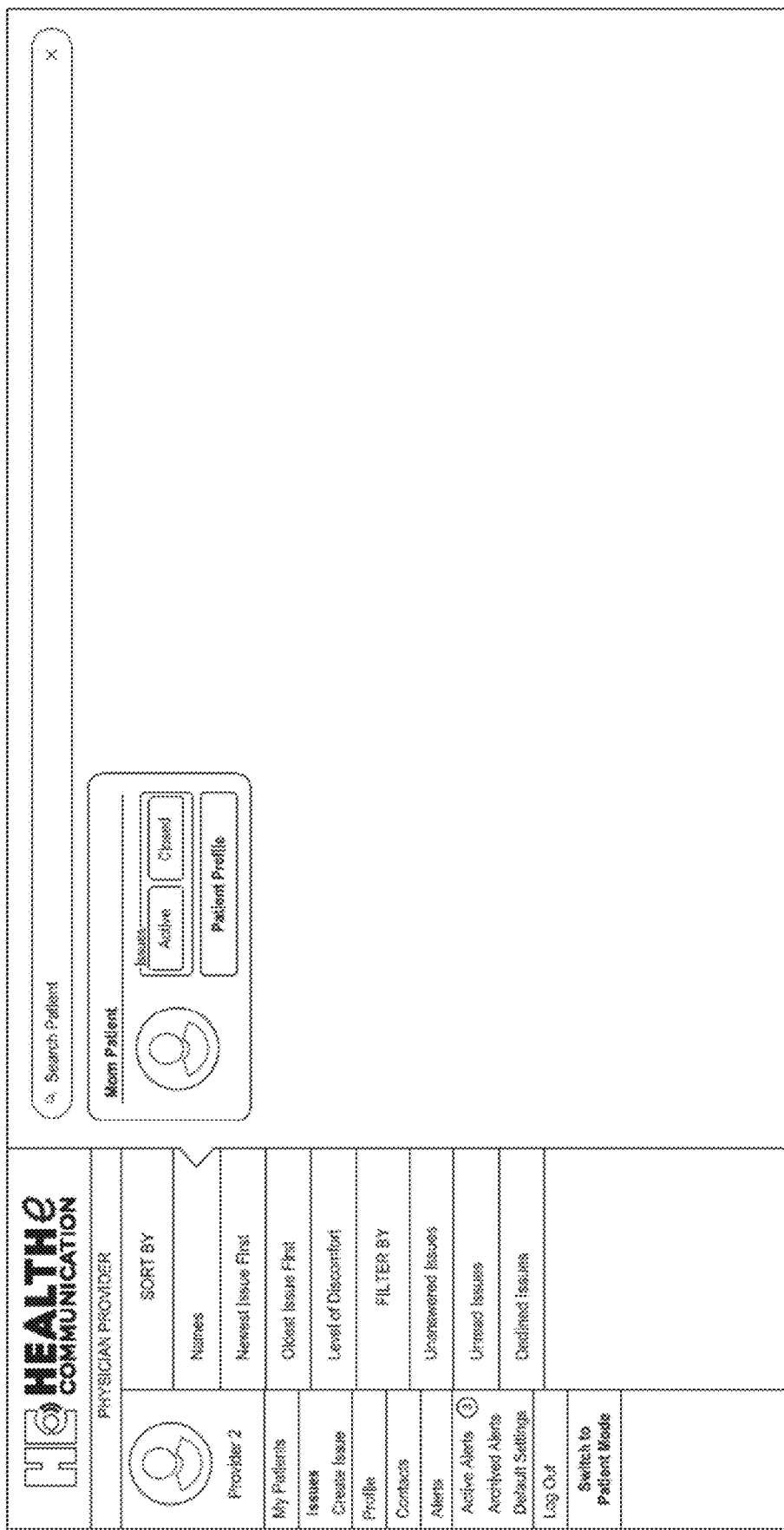
FIG. 13 illustrates an example provider main page view on a user interface or a portion thereof.
Figure 14:
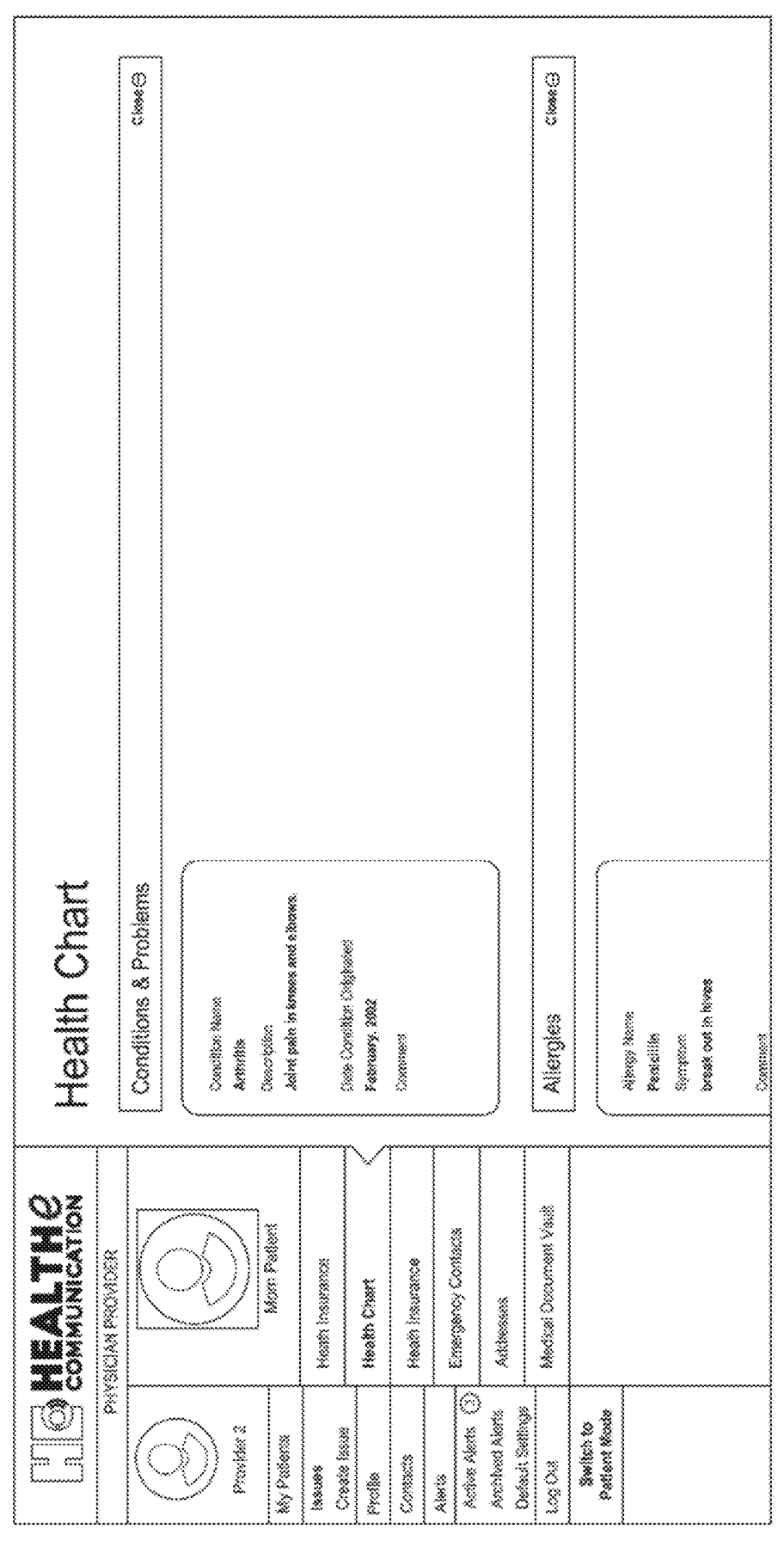
Figure 15:
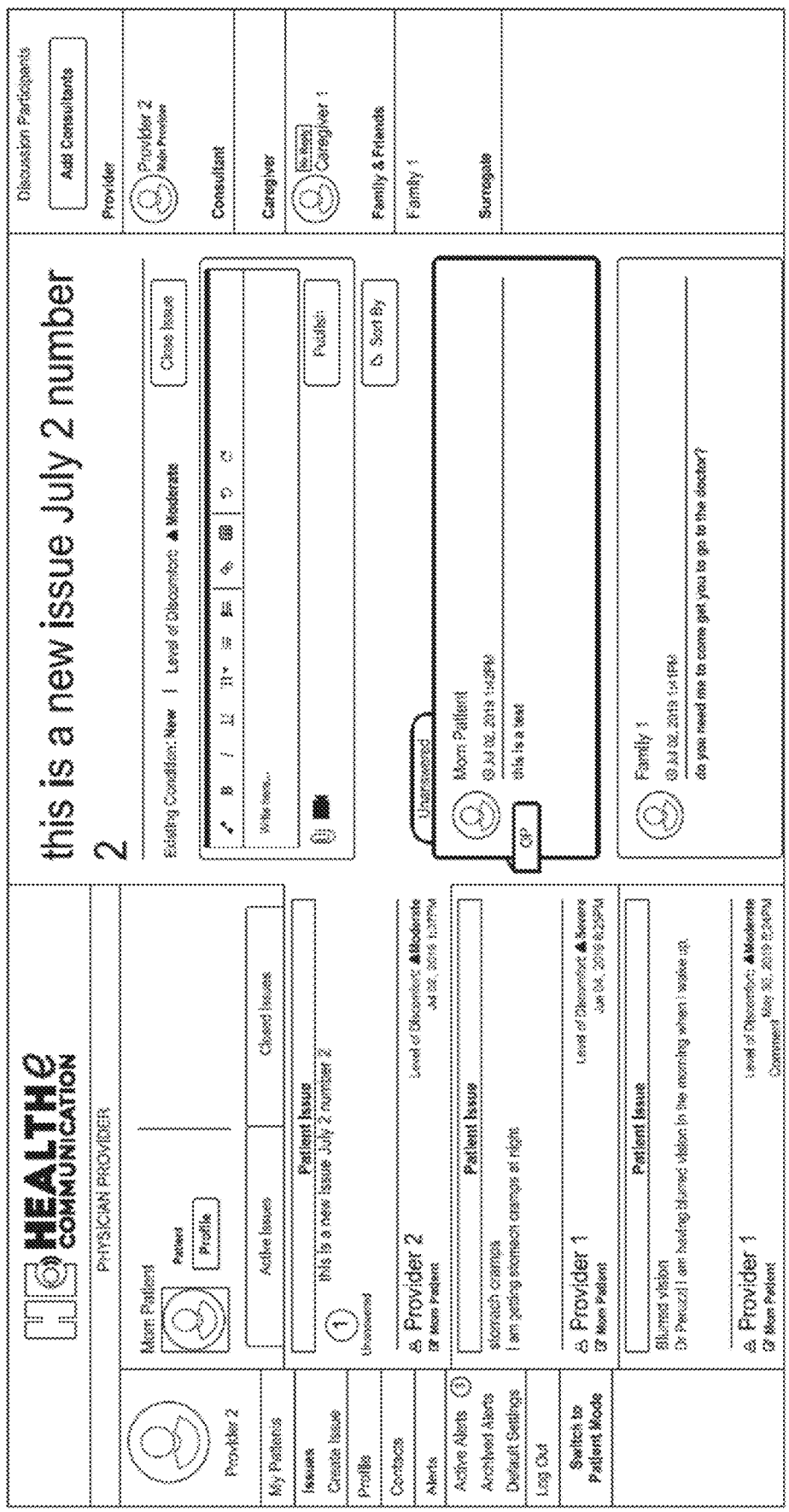
FIG. 15 illustrates an example provider view of the patient issue on a user interface or a portion thereof.
Figure 16:
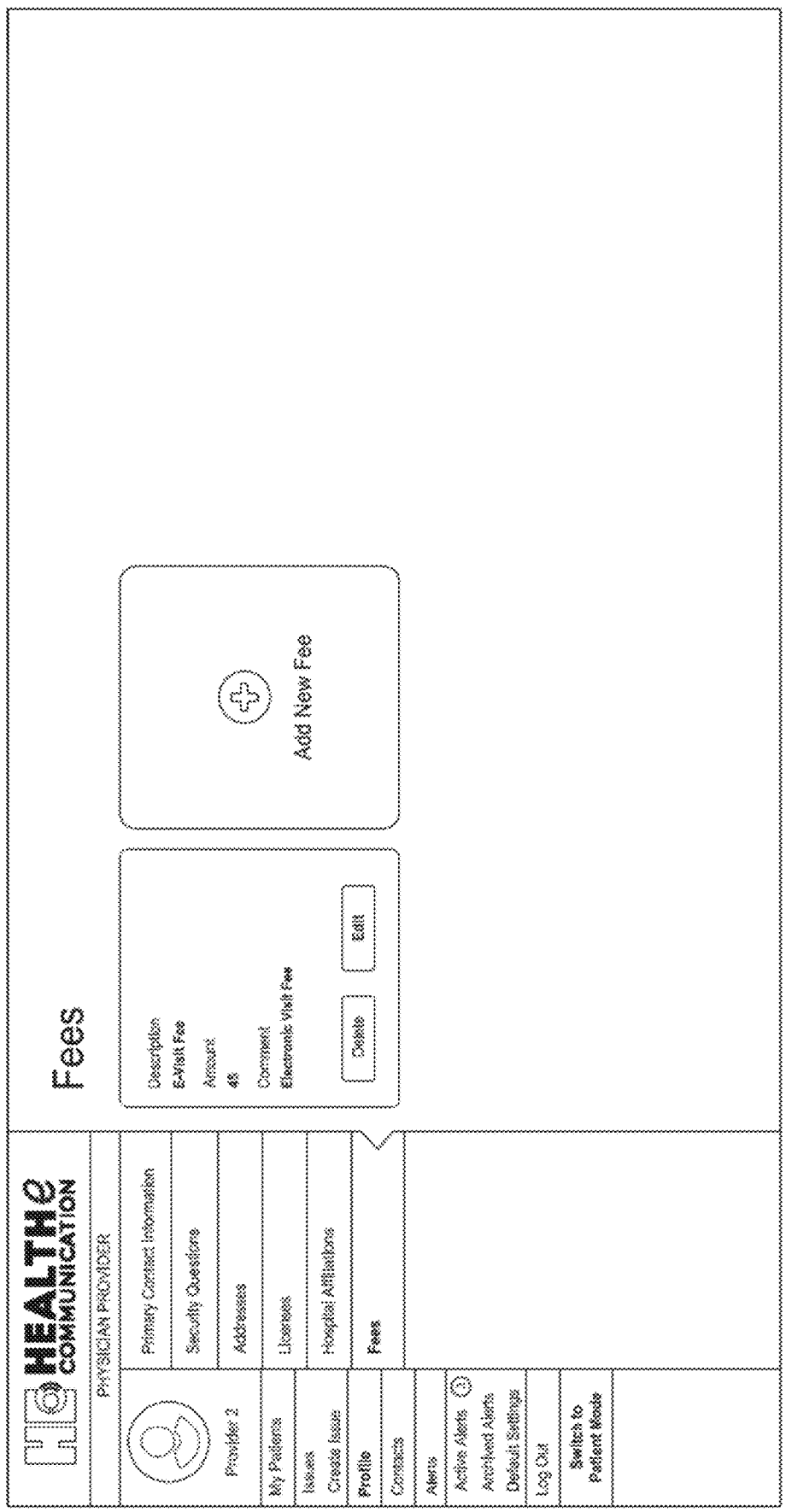
FIG. 16 illustrates example provider profile fees information on a user interface or a portion thereof.

FIGS. 13-16 illustrate example user interface displays of the system when the member is a provider. When a provider logs into the provider's account on the system, the patient's issues and/or different patients' issues can be sorted in a number of ways, for example, by the severity of trauma and/or condition (see FIG. 13), the level of pain experienced by the patient, the patient's name (see FIG. 13), the age of the patient, time that has lapsed since the issue was posted (see FIG. 13), and/or any of the combinations. The provider can selectively set his or her own preference of sorting. Additionally or alternatively, certain sorting criteria can be set as default and/or mandatory while other sorting criteria can be customized. As shown in FIG. 13, the provider can filter the issue invitations sent by the provider's patients. for example, by unanswered, unread, and/or declined issues. The provider can also organize group visits, for example, for patients with similar issues. The provider can click on the patient's profile to view information that the patient has given access to the provider, such as the patient's heath chart as shown in FIG. 14. As shown in FIG. 15, the provider can view the details of a patient's active issue. The provider may provide advice and/or ask follow-up questions after viewing the description of the issue (which may include photos and/or videos uploaded to that issue) and optionally additional information about that patient. As shown in FIG. 16, the provider may invoice and/or charge the patient after responding to the patient's active issue directly from the system. Optionally, the provider may only invoice and/or charge the patient after the provider has responded to the patient's active issue.

Figure 17:
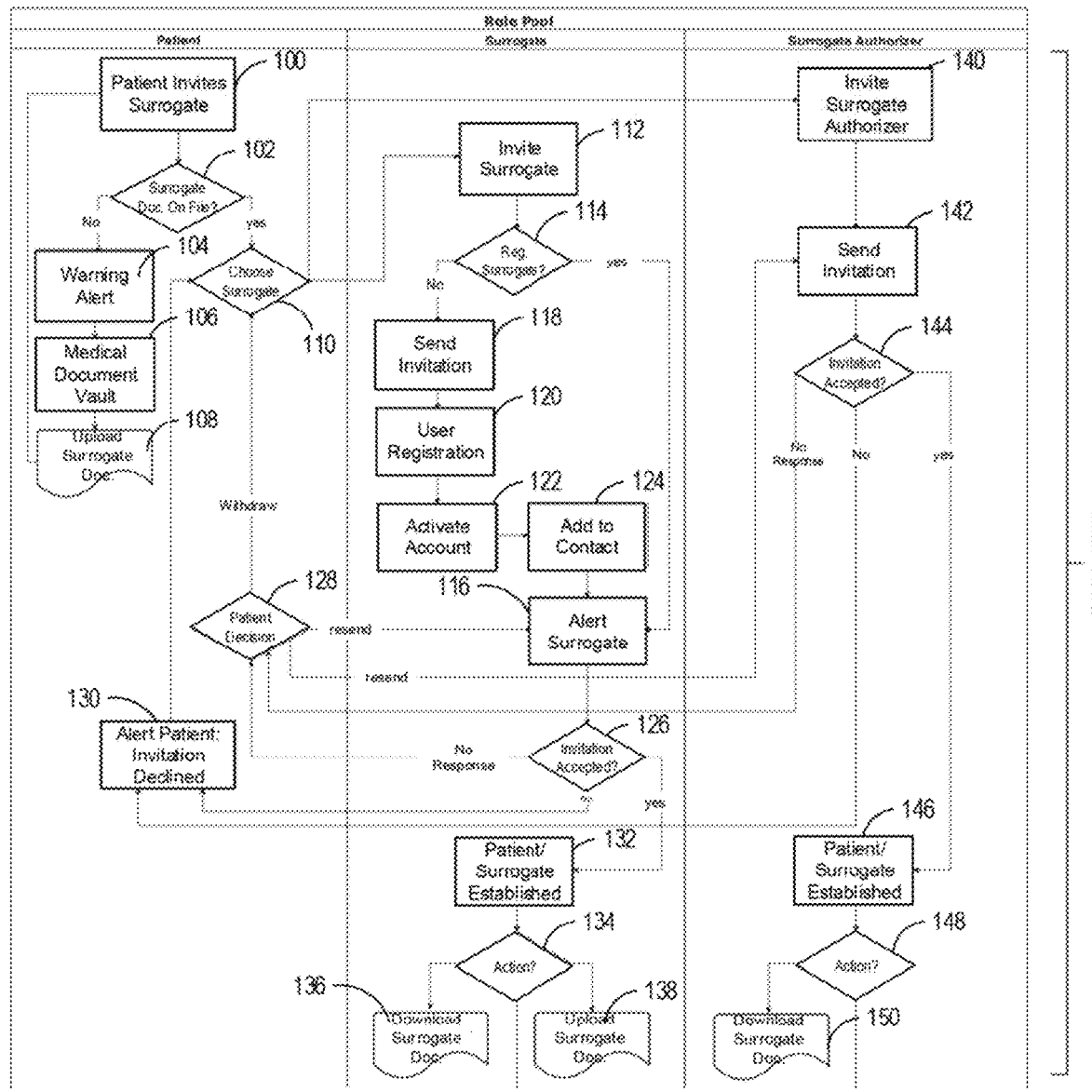
FIG. 17 illustrates an example surrogate assignment, authorization and/or activation process.
Figure 17:
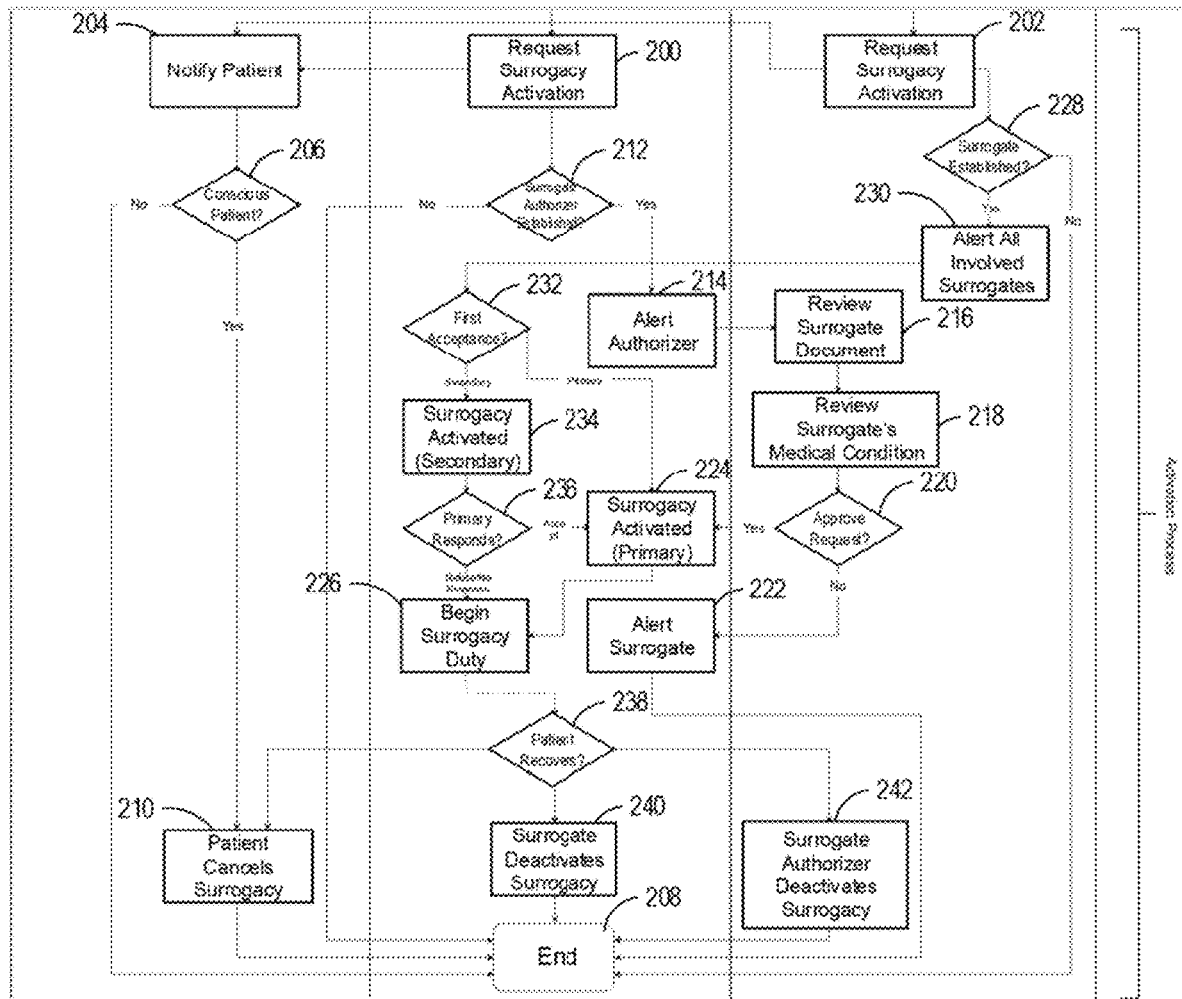

As described above, a patient may have appointed a surrogate, who can be a member of the system. FIG. 17 illustrates examples processes for authorizing surrogate control. In the present disclosure, surrogates may refer to any healthcare decision makers for the patient when the patient is unable to make decision for themselves. Surrogates can include, for example, parental surrogate, assigned surrogate, or medical power of attorney. A doctor or another medical personnel, also referred to as the surrogate authorizer, may need to certify that a surrogate is needed for a patient and/or approve the surrogate for the patient.

The processes in FIG. 17 can include an invitation process and an activation process. The invitation process can be initiated by the patient. At step 100, a processor of the system disclosed herein or of a separate surrogate control system can receive from a patient, who is a user of the example system disclosed herein, an invitation to a surrogate candidate. The processor can send an invitation an electronic message to a member's account, such as to the member's user device (for example, smartphone, tablet, laptop, and/or the like). The surrogate candidate can be from an established relationship, for example, next-of-kin, spouse, siblings, a previously assigned surrogate, or otherwise. At decision block 102, the processor can be instructed by the patient (by receiving an electronic message via the patient's account) to check whether the patient has a surrogate document on file. If there is no existing surrogate document, at step 104, the processor can output a warning alert. At step 106, the processor can redirect the patient to the patient's medical document vault page, such as the page shown in FIG. 6. After the processor receives an uploaded surrogate document (such as by the patient) at step 108, the process can return to step 100.

If there is already an existing surrogate document, at decision block 110, the processor can prompt the patient to decide whether the patient wants to choose a surrogate candidate, for example, from a list of existing surrogate candidates or otherwise. If the patient makes a selection of the surrogate candidate, the process can activate the process of inviting the surrogate candidate at step 112. At decision block 114, the processor can determine whether the surrogate candidate is registered in the system disclosed herein. If the surrogate candidate is registered, at step 116, the processor can send an invitation to the surrogate candidate and create a surrogate invitation alert. The processor can wait for action by the surrogate candidate. If the surrogate candidate is not registered, the processor can send a surrogate registration invitation email or a text message to the surrogate candidate at step 118. The surrogate candidate can register with the email link at step 120. The surrogate candidate can become a user of the system when the processor receives an account activation instruction at step 122 from the surrogate candidate. After the account is activated, at step 124, the processor can add the surrogate candidate to the patient's contact list automatically, for example to the patient's "Family & Friends" contact list or "Surrogate" contact list, or otherwise, and proceed to step 116 as described above.

At decision step 126, the processor can determine whether the surrogate candidate has accepted the invitation. If no response has been received from the surrogate candidate, the processor can proceed to decision step 128 to request patient decision. The patient can withdraw the invitation and return to decision block 110 to choose a different surrogate candidate. The patient can also alternatively instruct the processor to resend the invitation by returning to step 116. If the surrogate candidate has declined the invitation, the processor can proceed to step 130 to notify the patient of the decline by the surrogate candidate. The processor can then return to decision block 110 to request that the patient choose a different surrogate candidate.

If the surrogate candidate has accepted the invitation to become the surrogate to the patient, the processor can establish the patient/surrogate contact at step 132. The processor can then proceed to request actions from the surrogate at decision block 134. The processor can allow the surrogate to download a surrogate document at step 136 or upload a surrogate document at step 138. The surrogate can also standby for the surrogate activation process and request activation of the surrogacy at step 200 (described below) when the patient becomes incapacitated, such as when the patient is unconscious.

Additionally, in response to the processor's request at decision block 110, the patient can activate an invite surrogate authorizer process of the processor at step 140. At step 142, the processor can send an invitation to the surrogate authorizer and create a surrogate authorizer invitation alert. At decision block 144, the processor can determine whether the surrogate authorizer has responded to the invitation. If the surrogate authorizer has not responded, the processor can proceed to decision block 128 to request patient decision. The patient can withdraw the invitation and return to decision block 110 as described above, or resend the invitation by returning to step 142. If the surrogate authorizer has declined the invitation, the processor can proceed to step 130 to notify the patient of the decline by the surrogate authorizer. The processor can then return to decision block 110 to request that the patient choose a different surrogate authorizer.

If the surrogate authorizer has accepted the invitation to become the surrogate authorizer to the patient, the processor can establish the patient/surrogate authorizer contact at step 146. The processor can then proceed to request actions from the surrogate authorizer at decision block 148. The processor can allow the surrogate authorizer to download the surrogate document at step 150. The surrogate authorizer can also standby for the surrogate activation process and request activation of the surrogacy at step 202 (described below) when the patient becomes incapacitated, such as when the patient is unconscious.

The activation process can be initiated by the surrogate at step 200 or by the surrogate authorizer at step 202. In both cases, the processor can notify the patient of the surrogacy activation request at step 204. Upon notifying the patient, the processor can facilitate determination of whether the patient is conscious or otherwise incapacitated at decision block 206. The notification to the patient can act as a safety check. If the patient is not conscious and thus not able to respond to the notification, the processor can exit the safety check at step 208 and proceed to the activation process. The processor can deem the patient to be unconscious after no response is received within a predetermined time, such as 24 hours, 48 hours, or otherwise after sending the notification to the patient. If the patient is conscious, the patient can respond to the notification. If the patient believes the surrogacy activation was initiated in error, the processor can receive a cancelation of surrogacy from the patient at step 210 and exit the activation process at step 208.

Once the processor has received the surrogate's request to activate surrogacy at step 200, the processor can determine whether the patient has a surrogate authorizer at decision block 212. If a surrogacy authorizer has not been established for the patient, the processor can exit the activation process at step 208. If there is a surrogate authorizer, the processor can alert the surrogate authorizer to review the surrogate document at step 214. The processor can prompt the surrogate authorizer to review the surrogate's documents at step 216. The processor can prompt the surrogate authorizer to review the surrogate's clinical condition at step 218. The processor can request approval from the surrogate authorizer of the surrogate's request at decision block 220. If the request is denied, for example, if the patient does not need a surrogate, the processor can alert the surrogate at step 222 of the denial and exit the activation process at step 208. If the request is granted, surrogacy is activated at step 224.

Upon activation of surrogacy, the surrogate can log into the patient's account, such as the account on the system disclosed herein, to make decisions, for example, medical decisions, for the patient at step 226.

If the request to activate surrogacy is requested by the surrogate authorizer in step 202, the processor can determine whether a surrogate is available to the patient at decision block 228. If a surrogate has not been established for the patient, the processor can exit the activation process at step 208. If one or more surrogates have been established for the patient, the processor can be instructed by the surrogate authorizer to alert all the involved surrogates at step 230. At decision block 232, the processor can determine which surrogate accepts surrogacy first. The surrogate who accepts surrogacy first can be assigned as the active surrogate. If the active surrogate is the primary surrogate, the primary surrogacy can be activated at step 224 as described above. The primary surrogate can act as the controller of surrogacy. If the active surrogate is the secondary surrogate (i.e., the secondary surrogate is activated before the primary surrogate responds), the secondary surrogacy is established at step 234.

The secondary surrogate(s) can request, via the processor, a response from the primary surrogate at decision block 236. If the primary surrogate accepts the request from the secondary surrogate(s), surrogacy can be activated with the primary surrogate as the controller at step 224 as described above. In some embodiments, if the secondary surrogate is activated before the primary surrogate can act, when the primary surrogate responds, the primary surrogate replaces the secondary surrogate, and primary surrogacy can be activated at step 224. If the primary surrogate refuses to act or does not respond, the secondary surrogate(s) can log into the patient's account, such as the account on the system disclosed herein, to make decisions, for example, medical decisions, for the patient at step 226.

Optionally, after surrogacy has been activated, the patient recovers and wants to end surrogacy, sending such an instruction to the processor at decision block 238. The patient can cancel surrogacy at step 210. Alternatively or additionally, the surrogate can deactivate the surrogacy at step 240. Alternatively or additionally, the surrogate authorizer can deactivate the surrogacy at step 242.

Figure 18:
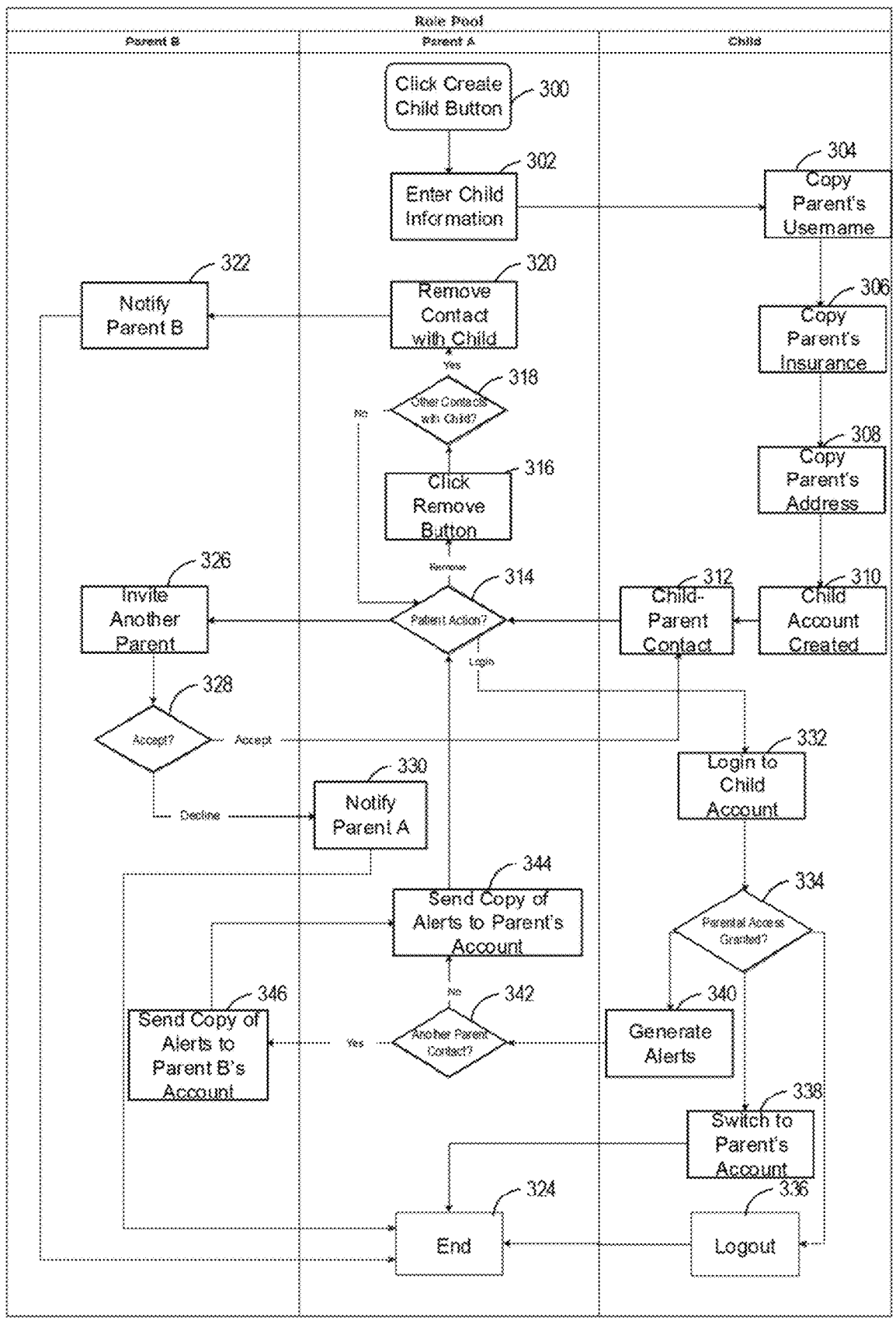
FIG. 18 illustrates an example process to facilitate the care of children patients by the children patients' parents and/or guardians.

FIG. 18 illustrates an example process of a child patient's parent or guardian initiating the care of the child patient. "Parent A" and "Parent B" are illustrative and non-limiting, and can refer to either a parent or a guardian (for example, a step-parent or otherwise) of the child patient. At step 300, Parent A can click the "create child" button or a similar button on the parent's account in the system described herein. The processor of the system can respond by prompting Parent A to enter the child's information, and receive the child's information at step 302. The processor can copy Parent A's username (which can be an email, a mobile number, or otherwise) at step 304 as instructed by the child. The processor can copy Parent A's health insurance data, or a portion thereof at step 306 as instructed by the child. The processor can copy Parent A's address at step 308 as instructed by the child. The processor can create the child's account at step 310 with the copied Parent A's information. The processor can create the child-Parent A contact at step 312. The linked account can be shown in Parent A's account, such as shown in FIG. 7, or in the child's account. Parent A can take action at decision block 314 on behalf of the child.

Parent A can remove the child-Parent contact at step 316, for example, by clicking "remove" or a similar button. The process can determine whether there is another parent-child contact at decision block 318. If there is another parent-child contact (for example, with Parent B), the processor can remove the child-Parent A contact at step 320. The processor can send Parent B a notification that Parent A has removed the contact with the child at step 322 and proceed to exit the process at step 324.

If there is no other parent-child contact, the processor can return to decision block 314 to ask Parent A for further action. Parent A can instruct the processor to invite one of the family and/or friends (for example, Parent B) to establish contact with the child at step 326. The processor can determine whether Parent B accepted or declined the invitation at decision block 328. If Parent B accepted the invitation, the processor can create the child-Parent B contact at step 312 as described above. If Parent B declined the invitation, the processor can send an alert to Parent A about the decline at step 330 and exit the process at step 324.

To take action on behalf of the child, when prompted to take action at decision block 314, the parent who has established contact with the child can log into the child's account at step 332. The processor can grant parental access to all the system functions at decision block 334. The parent can choose to log out of the account if no action is necessary at step 336 and the processor can exit the process at step 324. The parent can switch to the parent's own account at step 338 if no action is necessary on behalf of the child and the processor can exit the process at step 324. The processor can activate the system functions to generate alerts for the parent at step 340 if actions are needed for the child. When alerts are created, the processor can check whether there is another child-parent contact at decision block 342. If there is no other child-parent contact, the processor can send a copy of the alerts to the account of the parent who has contact with the child at step 344 and proceed to decision block 314 to request parent action as described above. If there is another established child-parent contact, at step 346, the processor can also send a copy of the alerts to the second parent (for example, Parent B)'s account. The second parent can instruct the processor to send a copy of the alerts to the first parent's account at step 344 as described above so that the first parent can take action on behalf of the child.

Figure 19:
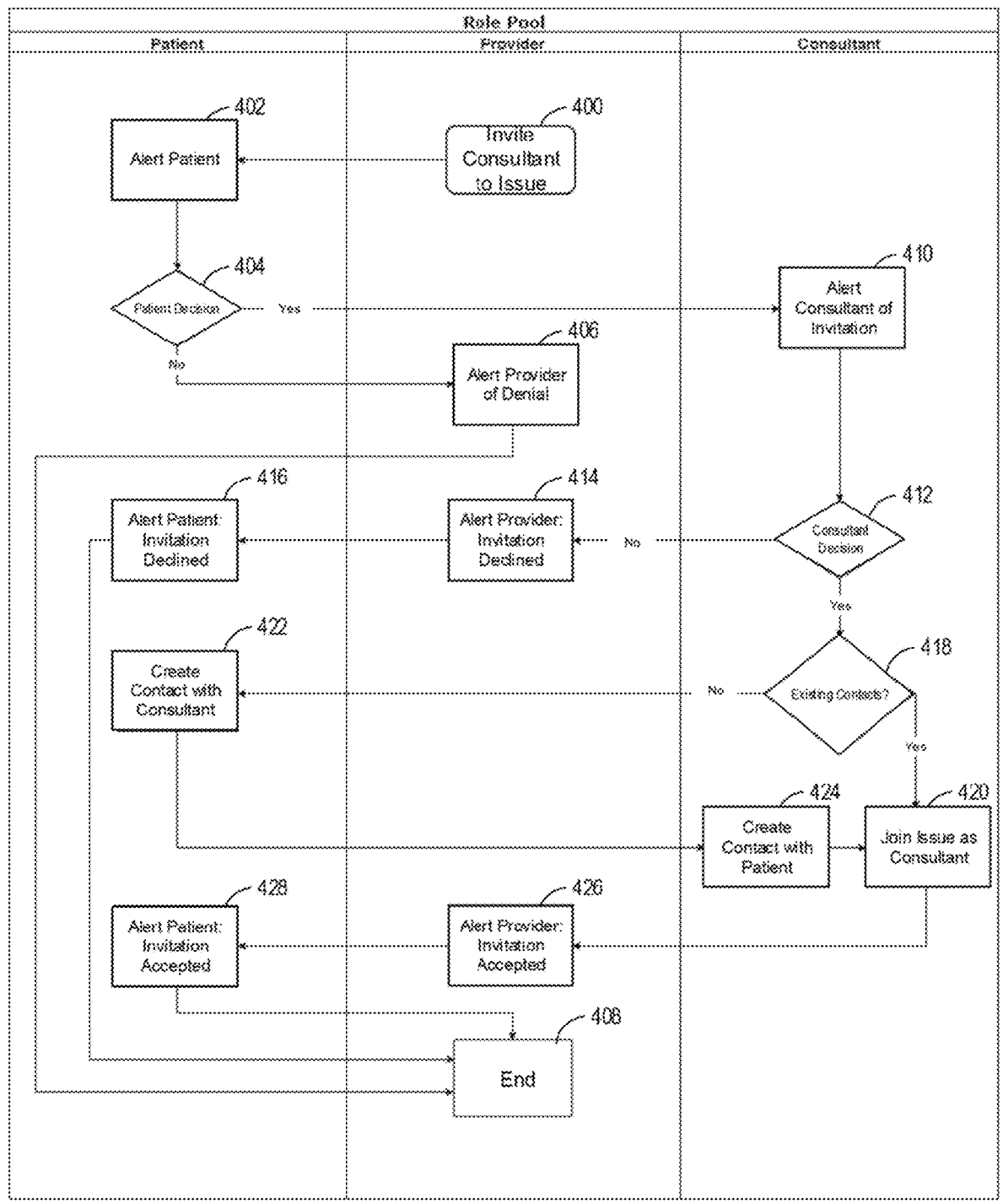
FIG. 19 illustrates an example process to allow providers to include additional clinicians into a discussion thread about a particular patient related issue.

As noted above, when caring for a patient, a provider may need to consult other healthcare professionals, who may have a different field of specialty from the provider and/or may have experiences related to the patient's health issue. FIG. 19 illustrates an example process to allow providers to include additional clinicians as the above-described consultant into a discussion thread about a particular patient related issue. The process can be initiated by the main provider, who can invite the consultant to an issue of the patient at step 400. At step 402, the processor can send an alert to the patient that a consultant has been invited. The processor can request the patient's permission at decision block 404. If the patient does not permit the invitation, the processor can send an alert to the provider at step 406. The processor can proceed to exit the process at step 408.

If the patient permits the invitation of the consultant, at step 410, the processor can send an alert regarding the invitation to the consultant. At decision block 412, the processor can determine the consultant's decision. If the consultant declined the invitation, at step 414, the processor can send an alert regarding the decline to the provider. At step 416, the processor can send an alert regarding the decline to the patient and proceed to exit the process at step 408.

If the consultant accepted the invitation, at decision block 418, the processor can determine whether there is an existing contact between the patient and the consultant (for example, the consultant already being a provider to the patient for a different issue). If there is an existing contact, at step 420, the processor can allow the consultant to join the patient's issue as a consultant. If there is no existing contact between the patient and the consultant, at step 422, the processor can create a provider-patient contact between the consultant and the patient on the patient's account. At step 424, the processor can create a provider-patient contact between the consultant and the patient on the consultant's account and proceed to join the consultant in the patient's issue as a consultant at step 420. Once the consultant has joined the issue, the processor can send an alert to the provider that the consultant has accepted the invitation at step 426. The processor can send an alert to the patient that the consultant has accepted the invitation at step 428. The processor can exit the process at step 408.

Figure 20:
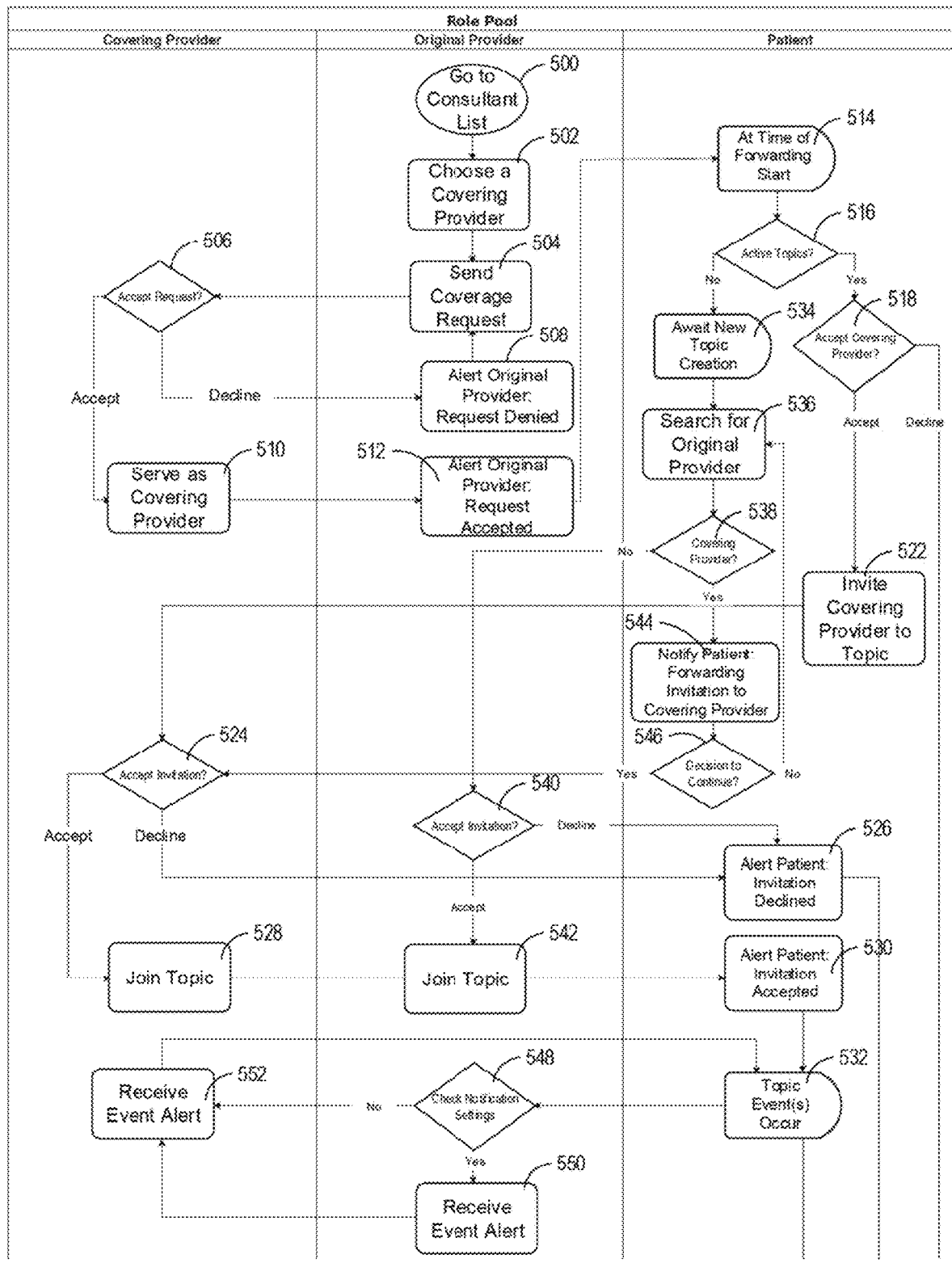
FIG. 20 illustrates an example process to allow a provider to forward messages to a colleague.
Figure 20:
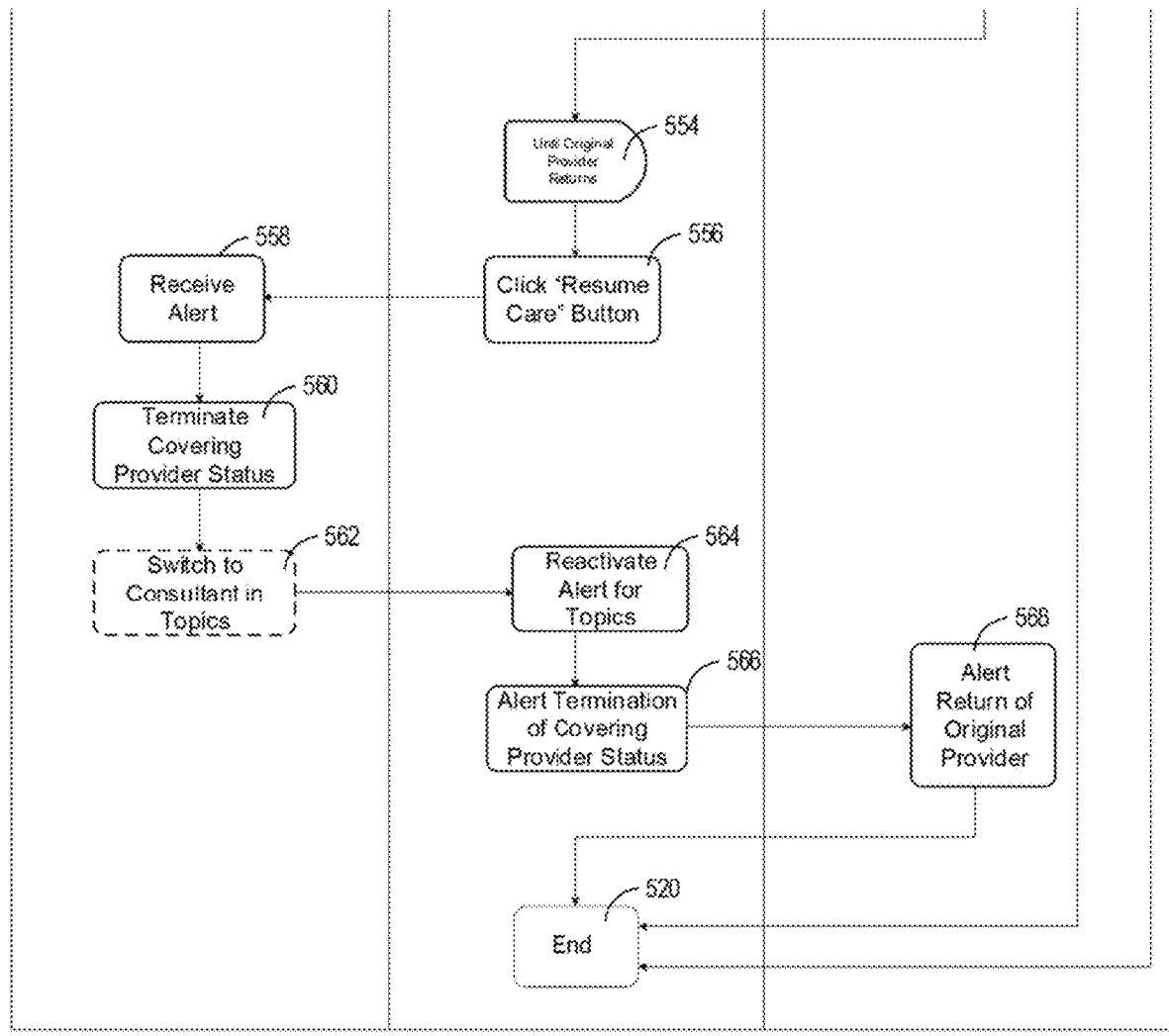

A primary care provider may not be available when a patient posts an active issue. For example, the provider may be away or otherwise indisposed. The provider may not be available for a period of time (such as more than several days, a week, several weeks, or several months) and/or not immediately available within the same day when the patient's issue is severe. FIG. 20 illustrates an example process performed by a processor of the integrated communication system to allow a provider to forward messages to a colleague when the provider is not available to care for the patient.

When a provider is expected to be unavailable to a patient for any period of time, at step 500, the processor can receive instructions from the provider to go to the consultant(s) list in the provider's contact list that is saved on the provider's account. At step 502, the processor can receive instructions from the provider to choose a colleague (or any other suitable healthcare provider) from the consultant(s) contact list as a covering provider when the original provider is not available. The provider may be unavailable for all patients and obtain coverage for each patient. Alternatively, the provider may be unavailable for one or more patients and obtain coverage for the affected patient(s). At step 504, the processor can send a coverage request from the original provider to the covering provider. For example, the original provider can click on a "Set as My Substitute" to send such a request. Upon receiving the coverage request on the covering provider's account, at decision step 506, the processor can receive instructions from the covering provider regarding whether to accept or decline the request. Upon receiving an instruction to decline the coverage request, the processor can proceed to step 508 to send an alert to the original provider that the request has been denied. The processor can return to step 504 to resend the coverage request. Alternatively, the processor can return to step 502 if the original provider selects a different covering provider. Upon receiving an instruction to accept the coverage request, the processor can proceed to step 510 to update the covering provider's account that this provider is serving as a covering provider for the original provider. The processor can then proceed to step 512 to send an alert to the original provider that the request has been accepted. After the acceptance of the coverage request by the covering provider, the system can standby until the time when the original provider is scheduled to be unavailable, that is, when the coverage starts at step 514. The processor can proceed to the patient's account at step 514.

In the patient's account, at decision step 516, the processor of the system can check whether there are any active health topics for that patient. The active topic can include any health conditions, including non-limiting examples such as the patient having high blood pressure, arthritis, diabetes, and/or the like. If there is currently at least one active topic on the patient's account, the processor can send an alert to the patient that the covering provider will be invited. At decision step 518, the processor can await the patient's instruction on whether to accept the covering provider. If the patient declines inviting the covering provider to the active issue topic, the processor can proceed to step 520 to exit the process. The patient can look for a different healthcare provider of the patient's choice.

If the patient accepts the covering provider to the topic, the processor can send an invitation to the covering provider to join the topic at step 522 from the patient's account. The covering provider's account can receive the topic invitation. At decision step 524, the processor can await the covering provider's instructions on whether to accept the topic invitation. If the covering provider declines the topic invitation, the processor can notify the patient that the invitation has been declined at step 526. The processor can then proceed to step 520 to exit the process. The patient can look for a different healthcare provider of the patient's choice. If the covering provider accepts the topic invitation, the processor can update the covering provider's account at step 528 to reflect that the covering provider has joined the topic. The processor can notify the patient that the invitation has been accepted at step 530. The covering provider can standby for when the topic events occur at step 532.

If the patient does not have any currently active health condition topics, that is, is the output to the decision step 516 is "No," the processor can standby at step 534 until the patient has created a new health topic. In response to the newly created topic, the processor can search for the patient's original provider at step 536, for example, from the patient's contacts list or otherwise. The processor can proceed to decision step 538 in response to the original provider being unavailable, to determine whether a covering provider has been appointed. If a coverage provider has been appointed, that is, if the output is "Yes" to decision step 538, the processor can proceed to step 544 to notify the patient that a topic invitation will be forwarded to the covering provider. At decision step 546, the processor can await the patient's decision to accept or decline the invitation forwarding. If the patient declines to forward the topic invitation to the covering provider, the processor can return to step 536 to search for another provider of the patient, for example, from the patient's contacts list. If the patient accepts forwarding of the topic invitation to the covering provider, the processor can proceed to decision step 524 to await the covering provider's decision to accept or decline the topic invitation.

If no covering provider has been appointed, that is, if the output is "No" to decision step 538, the processor can send a topic invitation to the original provider. At decision step 540, the processor can await instructions from the original provider on whether to accept the new topic invitation. If the original provider declines the invitation, the processor can notify the patient that the invitation has been declined at step 526. The processor can proceed to step 520 to exit the process. The patient can look for a different healthcare provider of the patient's choice. If the original provider accepts the topic invitation (for example, if the original provider become available when the new topic is created), the processor can update the original provider's account at step 542 to reflect that the original provider has joined the topic. The processor can notify the patient that the invitation has been accepted at step 530. The original provider can standby for when the topic events occur at step 532.

When one or more topic events occur at step 532 (for example, when the patient reports pain and/or discomfort due to the health conditions in an active topic), the processor can first check the original provider's notification settings at decision step 548. If the original provider has set up notifications to be sent to both the original provider and the covering provider, the processor can send an alert of the topic event(s) to the original provider at step 550 and to the covering provider at step 552. If the original provider has set up notification to be sent only to the covering provider while the original provider is unavailable, the processor can send an alert of the topic event(s) only to the covering provider at step 552. The covering processor can address the topic event(s) upon receiving the alert. When additional or new topic event(s) occur, the processor can repeat the steps 548, 550, and 552. The processor can repeat these steps until the original provider changes the status of the original provider to be available again at step 554.

After the original provider's return at step 554, the processor can receive instructions from the original provider to resume care at step 556. For example, the original provider can click a "Resume Care" button to update the original provider's availability on the original provider's account. The processor can send an alert to the covering provider that the original provider can resume care at step 558. In response to the alert, the covering provider can update the account to terminate the covering provider's status for the particular patient at step 560. The termination can include terminating the forwarding process of the patient's active topics to the covering provider. Optionally, at step 562, the covering provider can switch the relationship with the patient to a patient-consultant contact in the covered topics. After the covering provider has stopped acting as the provider for the patient, at step 564, the processor can reactivate the alert to the original provider for the patient's covered topics. The processor can also alert the original provider that the covering provider has terminated the forwarding process at step 566. The processor can also alert the patient that the original provider has resumed care of the patient at step 568. The processor can proceed to step 520 to exit the process.

Figure 21:
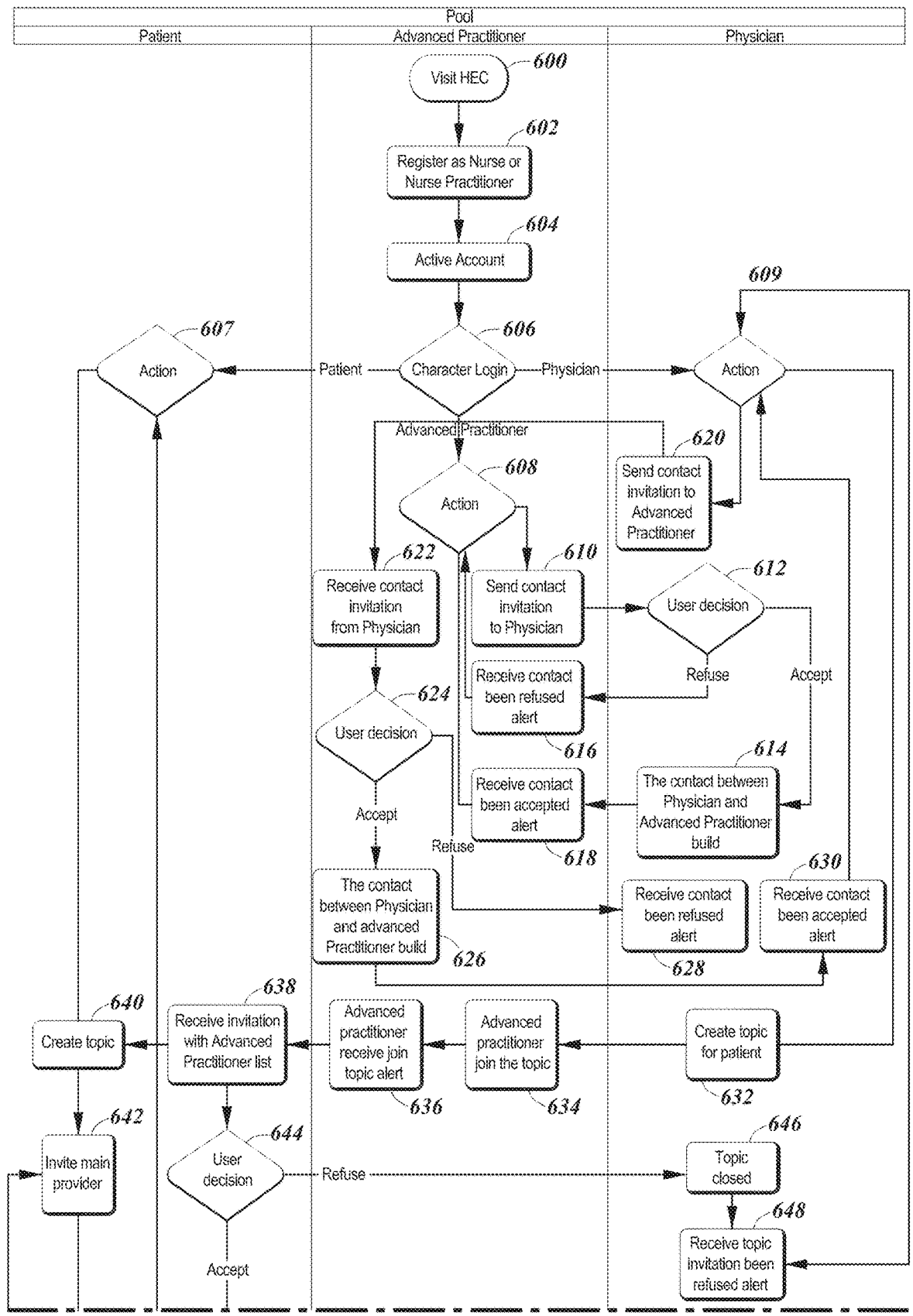
FIG. 21 illustrates an example process for authorizing an advanced practitioner and/or a physician's control.
Figure 21:
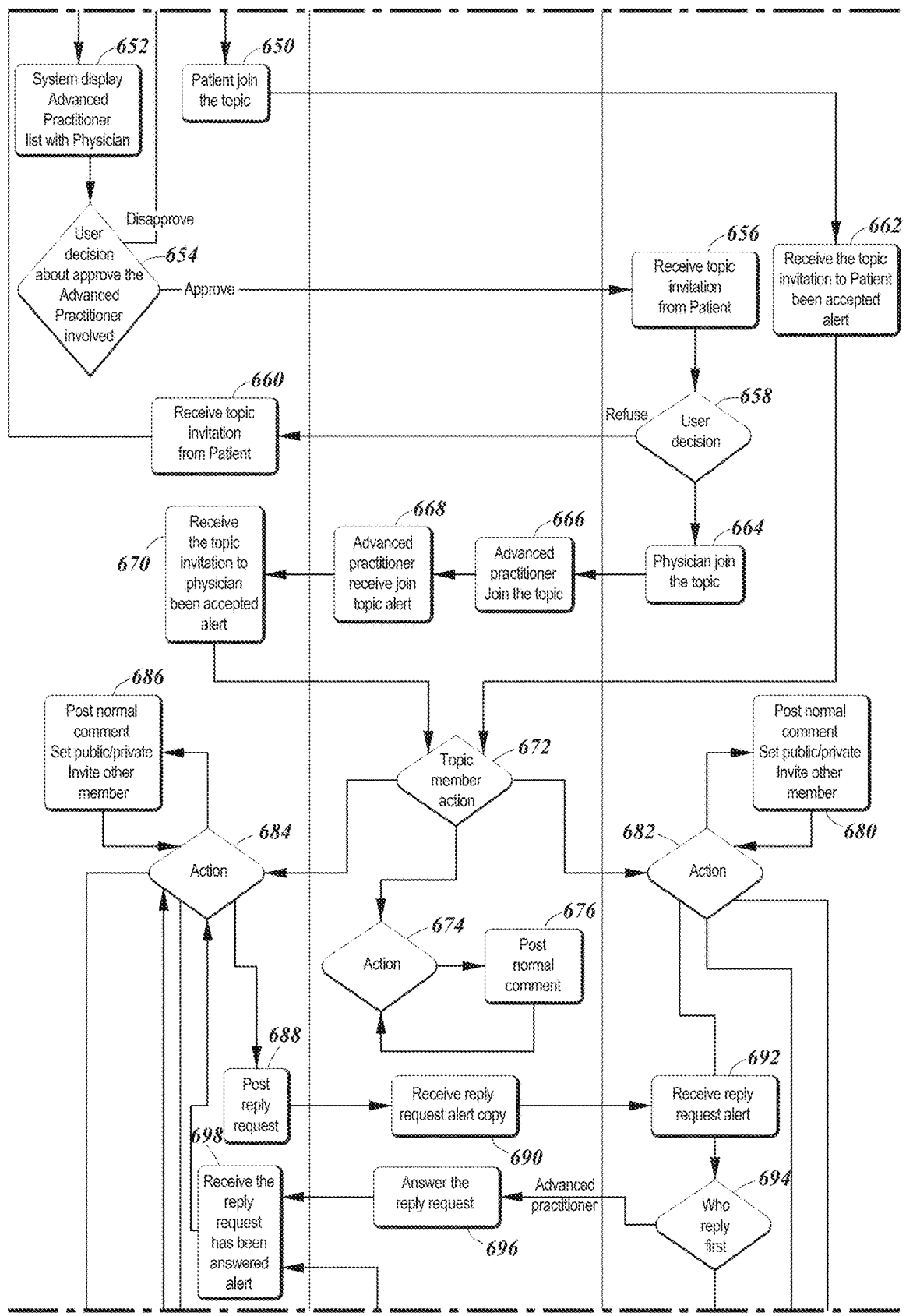
Figure 21:
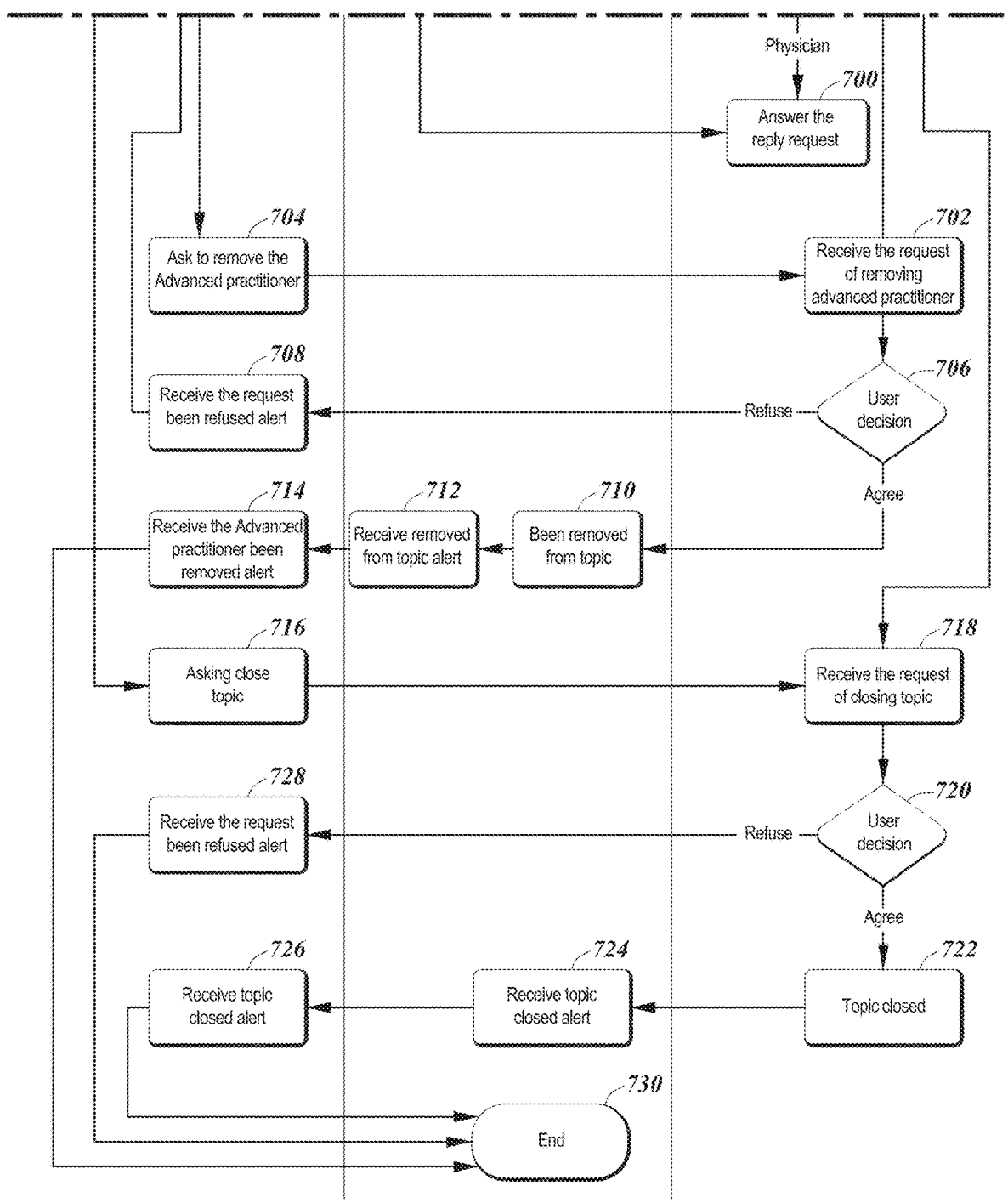

In some situations, a physician and/or a patient can appoint an advanced practitioner to be a member of the system. FIG. 21 illustrates examples processes for authorizing an advanced practitioner control. In the present disclosure, advanced practitioner may refer to a caregiver or a nurse. At step 600, the advanced practitioner can visit the processor of the present disclosure, register at step 602 and create an active account at step 604. At decision block 606, once logged in, the advanced practitioner's profile can be sent to a patient at decision block 607 and a physician at step 609. The advanced practitioner can also proceed to decision block at step 608 where the advanced practitioner can send a contact invitation to Physician at step 610.

As discussed above, the advanced practitioner's character login can be sent to the physician at step 609. The physician can send contact invitation to the advanced practitioner at step 620 which the advanced practitioner can receive at step 622. The advanced practitioner can then make a decision at decision block 624 as to whether accept or deny the contact invitation from the physician. If the advanced practitioner accept the contact invitation from the physician, then the system can establish the contact between the physician and advanced practitioner at step 626 and the physician can receive an alert at step 630 that the contact between the physician and the advanced practitioner is accepted. The physician can proceed to create a topic for patient at step 632. If the advanced practitioner refuses to accept the invitation from the physician, the physician can receive an alert at step 628 that the advanced practitioner has refused the contact invitation. Similarly, and/or alternatively, the advanced practitioner can send contact invitation to physician at step 610, and the physician can decide whether to accept or refuse the contact invitation at decision block 612. If the physician refuses to accept the contact invitation from the advanced practitioner, the advanced practitioner can receive an alert at step 616 at which point the advanced practitioner can decide whether or not to initiate another contact invitation to the physician. If the physician accepts the contact invitation from the advanced practitioner, the system can establish the contact between the physician and the advanced practitioner at step 614, and the advanced practitioner can receive an alert at step 618 that the contact has been accepted.

As discussed above, the advanced practitioner's character login can be sent to the patient. At decision block 607, the patient can decide whether to proceed with creating a topic. The topic can be a health or medical issue that the patient is concerned about. The patient can create more than one topic if the patient wishes to have different group of people involved in each topic discussion. If the patient chooses to create a topic, the system can take the patient to step 640 where the patient can do so, and then proceed to inviting the main provider (e.g., primary healthcare provider) at step 642. The system can then display the advanced practitioner list with the physician at step 652. The patient can have the ability to decide at decision block 654 as to whether to approve or disapprove the advanced practitioner in the topic. This can provide a benefit for the patient to be in control of their health data and be able to approve or disapprove other people that can have access to information shared in a certain topic.

The topic can be created by the patient, as discussed earlier with respect to step 640, or the physician can create the topic for the patient, such as at step 632. If the physician creates the topic, the physician can send the topic to the advanced practitioner where the advanced practitioner can join at step 634 and receive an alert to join at step 630. Once the patient receives invitation with advanced practitioner list at step 638, the patient can decide, at decision block 644, whether to accept and join the topic at step 650 or refuse to join the topic. This feature allows the patient to be in control of the topic the patient wants to be involved in and the people that can be involved in each topic even if the topic is initiated by the physician. If the patient decides to refuse to join the topic, the topic can be closed at step 634 and the physician can be alerted at step 648 that the patient has refused to accept the topic invitation.

The physician can be notified as to whether the patient is prepared to join a topic with an advanced practitioner. This notification can occur whether the patient or the physician created the topic. For example, if the patient creates the topic, the physician can be alerted at step 656 and receive a topic invitation from the patient. The physician can then decide whether to join the topic at decision block 658. If the physician refuses to join the topic, the patient can be alerted at step 660 at which point the patient can create another invite to the main provider and repeat steps 642, 652, and 654 until the physician accepts the topic invitation from the patient. Once the physician decides to accept to join the topic at decision block 658, the physician can join the topic at step 664 followed by advanced practitioner joining the topic at step 666 and receiving a join topic alert at step 668. The patient can then receive an alert that the topic invitation to physician has been accepted. At this stage, the physician, the advanced practitioner, and the patient become members of the topic and can take certain actions at step 672. On the other hand, if the physician creates the topic, once the patient joins the topic at step 650, the physician can receive a notification at step 662 that the topic invitation to patient has been accepted. After that, the physician, the advanced practitioner, and the patient are all members of the topic and can take certain actions at step 672.

The patient can take certain actions at step 684 once the patient is a topic member. For example, at step 686, the patient can post normal comments, invite other members, and/or adjust the privacy settings for a topic to be public or private and repeat any of these actions as need be. The patient can also take other actions that can involve the physician and/or the advanced practitioner. For example, at step 688, the patient can request a reply regarding a certain topic. The physician receives the reply request alert from the patient at step 692 while the advanced practitioner can receive a copy of the alert that the patient has requested a reply. This can allow the physician (rather than the advanced practitioner) to decide at decision block 694 whether the advanced practitioner or the physician should reply to the patient's inquiry first.

The decision block 674 at the initial stage of the advanced practitioner becoming a topic member only allows the advanced practitioner to take certain actions. The advanced practitioner can post normal comments at step 676 and repeat this process. On the other hand, the decision block 682 can allow the physician to take more actions at this stage. For example, the physician can post normal comments, invite other members, and/or adjust the privacy settings for a topic to be public or private and repeat any of these actions as need be. The physician can also attend to a reply request from the patient at step 692 at which point the physician can decide at decision block 694 whether the physician or the advanced practitioner should reply first. If the physician decides that the advanced practitioner should reply first, the advanced practitioner can reply to the patient's request at step 696 which subsequently notifies the patient that the reply request has been answered at step 698. The patient can repeat this process at step 684 by posting another reply request. If the physician decides that the physician should answer the reply request, the physician can do so at step 700 which subsequently alerts the patient at step 698 that the patient's reply request has been answered. The patient can repeat this process at step 684 by posting another reply request.

The patient can continue to manage the advanced practitioner's access to a particular topic even after the advanced practitioner becomes a topic member. For example, at step 704, the patient can ask to remove the advanced practitioner from the topic discussion. The request can be directed to the physician who can decide, at decision block 706, whether to agree with the patient's request or refuse it. If the physician refuses to remove the advanced practitioner from the topic, the patient can receive an alert at step 708 at which point the patient can repeat the process by, for example, initiating another request at step 704 to remove the advanced practitioner. On the other hand, if the physician agrees to remove the advanced practitioner, the advanced practitioner can be removed from the topic at step 710 and receive an alert, indicating as such at step 712. The patient can subsequently be alerted at step 714 that the advanced practitioner has been removed from the topic which ends this particular process at step 730.

The patient can initiate a request to close a certain topic at step 716. For example, if the patient no longer feels the need to seek medical advice or if the patient's symptoms have already cleared, the patient can initiate such request at step 716 which is then routed to the physician at step 718 to decide whether the topic can be closed or not. If the physician refuses to close the topic, the patient can receive an alert at step 728. The topic can remain open which ends this particular process at step 730. On the other hand, if the physician decides, at step 720, that a particular topic can be closed, the topic can be closed at step 722. Both the advanced practitioner (at step 724) and the patient (at step 726) can receive a notification that the topic has been closed, which ends this particular process at step 730.

Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor comprising digital logic circuitry, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may." "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A secured database system, the system configured to receive data related to provider communications in forms of text, audio, and/or video messages, the system comprising:
    a processor configured to encrypt the data to output encrypted data and decryption keys upon receiving the data in a first virtual communication room from a first registered user's device when the first registered user is logged into the system on the first registered user's device, the first virtual communication room created by the processor being specific to a first health issue of the first registered user, the first registered user being a patient, wherein the processor is configured to create a new virtual communication room for each new health issue of the first registered user, and wherein:
        in response to an access request from a second registered user's device received at a first server when the second registered user is logged into the system on the second registered user's device, the second registered user being a healthcare provider, the processor is configured to deny access of the second registered user to the data until the second registered user has received and accepted an invitation message from the first registered user to join the first virtual communication room,
        the processor is further configured to deny access of the second registered user to the new virtual communication room unless the first registered user sends a separate invitation message for the new virtual communication room to the second registered user and the second registered user accepts the separate invitation message,
        the processor is further configured to allow the second registered user to invite a third registered user to join the first virtual communication room only after the first registered user accepts a request from the second registered user to invite the third registered user to join the first virtual communication room, the third registered user being a second healthcare provider such that the processor is configured to allow the second healthcare provider to respond to an inquiry by the first registered user in the virtual room with authorization from the healthcare provider, and
        the processor is further configured to check a notification setting of the second registered user's account upon receiving a status update that the second registered user will be available, the notification setting including whether an alert about the first registered user's first health issue should be sent to only to the third registered user or to both the second registered user and the third registered user; the system further comprising:
    the first server including a first memory device configured to store information of the first virtual communication room including the encrypted data, the first server being a remote server; and a second server including a second memory device configured to store the decryption keys, the second server being a local server, wherein in response to the second registered user having accepted the invitation message and the first server receiving the access request from the second registered user's device, the first server is configured to send a request to the second server to retrieve the decryption keys so as to decrypt the encrypted data, the second registered user being able to view decrypted data on the second registered user's device, the decrypted data not being stored on the second registered user's device.

2. The system of claim 1, wherein the first server is a cloud-based server.

3. The system of claim 1, wherein the processor is configured to send a notification alert to the second registered user on a mobile device without requiring the second registered user to log into the system on the mobile device, the notification being sent based on a category of a medical condition that is reported by the first registered user in the first virtual communication room.

4. The system of claim 1, wherein the processor is configured to automatically log out the first registered user or the second registered user after a period of inactivity of the respective user.

5. The system of claim 4, wherein the period of inactivity is about five minutes.

6. The system of claim 1, wherein the processor is further configured to allow the first registered user to invite a third registered user to join the first virtual communication room, the third registered user being a family member of the first registered user.

7. A method of providing secured communication using a secured database system, the method comprising:

using a processor of the secured database system:

creating a first virtual communication room specific to a first health issue of a first registered user upon instructions from a first registered user's device when the first registered user is logged into the system on the first registered user's device, the first registered user being a patient;

creating a new virtual communication room for each new heath issue of the first registered user;

receiving data in forms of text, audio, and/or video messages;

encrypting the data to output encrypted data and decryption keys upon receiving the data in the first virtual communication room from the first registered user's device;

storing information of the first virtual communication room including the encrypted data on a first memory device of a first server, wherein the first server is a remote server;

storing the decryption keys on a second memory device of a second server, wherein the second server is a local server;

denying access of a second registered user to the data until the second registered user has received and accepted an invitation message from the first registered user to join the first virtual communication room;

denying access of the second registered user to the new virtual communication room unless the first registered user sends a separate invitation message for the new virtual communication room to the second registered user and the second registered user accepts the separate invitation message; and in response to an access request from a second registered user's device received at the first server when the second registered user is logged into the system on the second registered user's device, the first server is configured to send a request to the second server to retrieve the decryption keys so as to decrypt the encrypted data, the second registered user being able to view decrypted data on the second registered user's device, the decrypted data not being stored on the second registered user's device;

wherein the processor is configured to allow the second registered user to invite a third registered user to join the first virtual communication room only after the first registered user accepts a request from the second registered user to invite the third registered user to join the first virtual communication room, the third registered user being a second healthcare provider such that the processor is configured to allow the second healthcare provider to respond to an inquiry by the first registered user in the virtual room with authorization from the healthcare provider, and wherein the processor is further configured to check a notification setting of the second registered user's account upon receiving a status update that the second registered user will be available, the notification setting including whether an alert about the first registered user's first health issue should be sent to only to the third registered user or to both the second registered user and the third registered user.

8. The method of claim 7, wherein the first server is a cloud server.

9. The method of claim 7, further comprising sending a notification alert to the second registered user on a mobile device without requiring the second registered user to log into the system on the mobile device, the notification being sent based on a category of a medical condition that is reported by the first registered user in the first virtual communication room.

10. The method of claim 7, further comprising automatically logging out the first registered user or the second registered user after a period of inactivity of the respective user.

11. The method of claim 10, wherein the period of inactivity is about five minutes.

12. The method of claim 7, wherein the second registered user is a family member of the first registered user.

* * * * *